(12) United States Patent
Karazincir et al.

(10) Patent No.: US 11,137,334 B2
(45) Date of Patent: Oct. 5, 2021

(54) SYSTEMS AND METHODS FOR FRACTURE FACE FORMATION PERMEABILITY MEASUREMENTS

(71) Applicant: Chevron U.S.A. Inc., San Ramon, CA (US)

(72) Inventors: Oya Aysen Karazincir, Houston, TX (US); Yan Li, Bellaire, TX (US); Karim Shafik Zaki, Houston, TX (US); Wade H. Williams, Cypress, TX (US); Ruiting Wu, Sugar Land, TX (US); Yunhui Tan, Houston, TX (US); Margaretha Catharina Maria Rijken, Houston, TX (US); Russell Thomas Ewy, San Ramon, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 202 days.

(21) Appl. No.: 16/452,111

(22) Filed: Jun. 25, 2019

(65) Prior Publication Data

US 2019/0391065 A1   Dec. 26, 2019

Related U.S. Application Data

(60) Provisional application No. 62/689,617, filed on Jun. 25, 2018.

(51) Int. Cl.
*G01N 15/08*        (2006.01)
*G01N 33/24*        (2006.01)

(52) U.S. Cl.
CPC ........... *G01N 15/082* (2013.01); *G01N 33/24* (2013.01); *G01N 15/0826* (2013.01)

(58) Field of Classification Search
CPC ...... G01N 15/00; G01N 15/08; G01N 15/082; G01N 15/0826
See application file for complete search history.

(56) References Cited

U.S. PATENT DOCUMENTS

2008/0134760 A1*   6/2008   Egermann .............. G01N 33/24
                                                                73/38
2014/0288909 A1    9/2014   Prestwood et al.
(Continued)

OTHER PUBLICATIONS

Karazincir, Oya, et al.; "Measurement of Reduced Permeability at Fracture Face Due to Proppant Embedment and Depletion"; (Sep. 2018), SPE-191653-MS, pp. 1-16.

*Primary Examiner* — Nguyen Q. Ha

(57) ABSTRACT

In some embodiments, a system includes a housing having a cavity defined therein for holding a test sample, a first inlet in fluid communication with the cavity to deliver fluid to the test sample, a second inlet in fluid communication with the cavity to deliver fluid to the test sample, the first inlet configured to deliver fluid to the test sample in a direction substantially perpendicular to a direction that the second inlet is configured to deliver fluid to the test sample, an outlet in fluid communication with the cavity to receive fluid from the test sample, and a force applicator configured to apply compressive force to the test sample within the cavity. The force applicator forms a seal with the housing while applying compressive force to the test sample. The system also comprises at least one sensor configured to, while fluid flows from at least one of the inlets through the test sample to the outlet, determine a fluid characteristic, a test sample characteristic, or any combination thereof.

22 Claims, 29 Drawing Sheets

(56) References Cited

U.S. PATENT DOCUMENTS

| | | | |
|---|---|---|---|
| 2015/0059447 A1* | 3/2015 | Rickards | G01N 19/00 73/61.41 |
| 2017/0058186 A1 | 3/2017 | Oghena et al. | |
| 2018/0335374 A1* | 11/2018 | Kanj | G01N 15/0826 |
| 2019/0226970 A1* | 7/2019 | Dusterhoft | E21B 49/00 |
| 2019/0317005 A1* | 10/2019 | Acosta | E21B 41/00 |

* cited by examiner

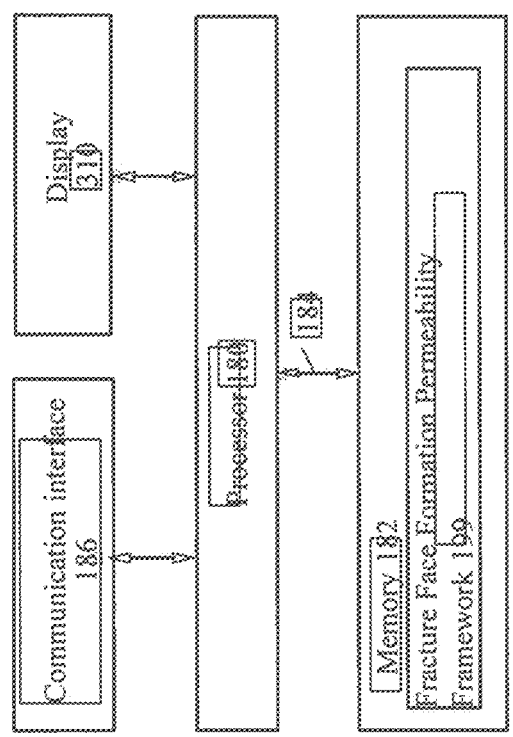

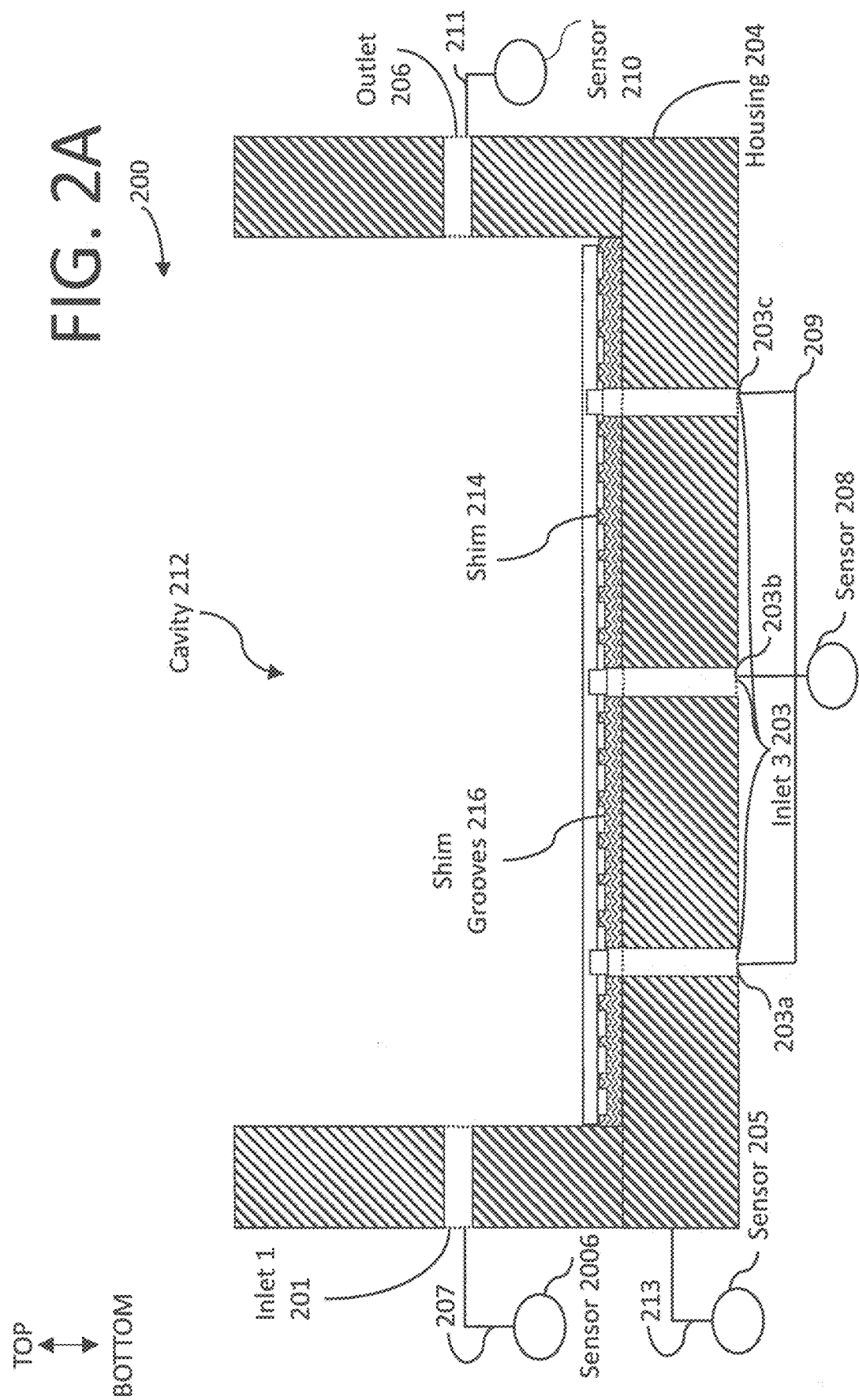

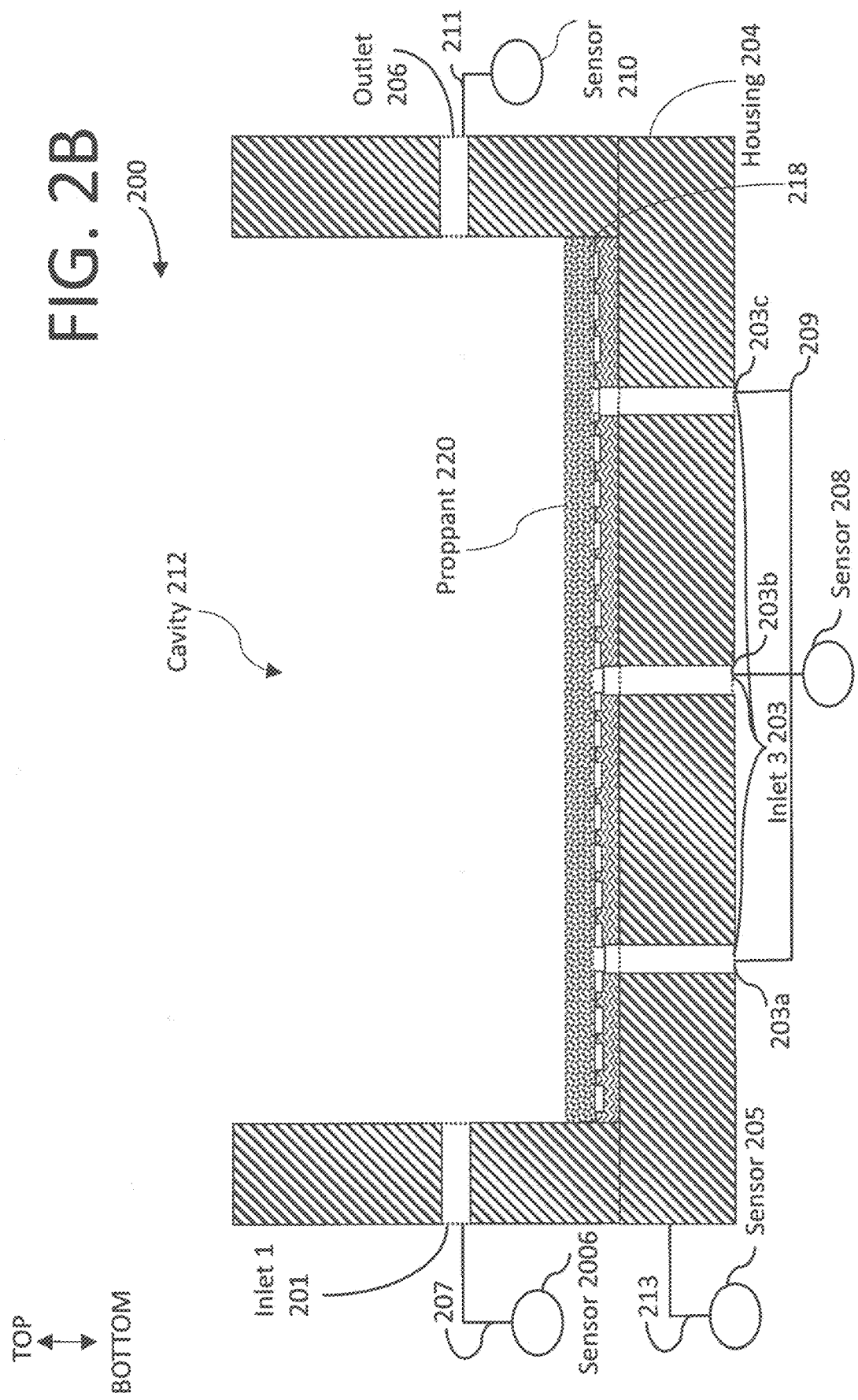

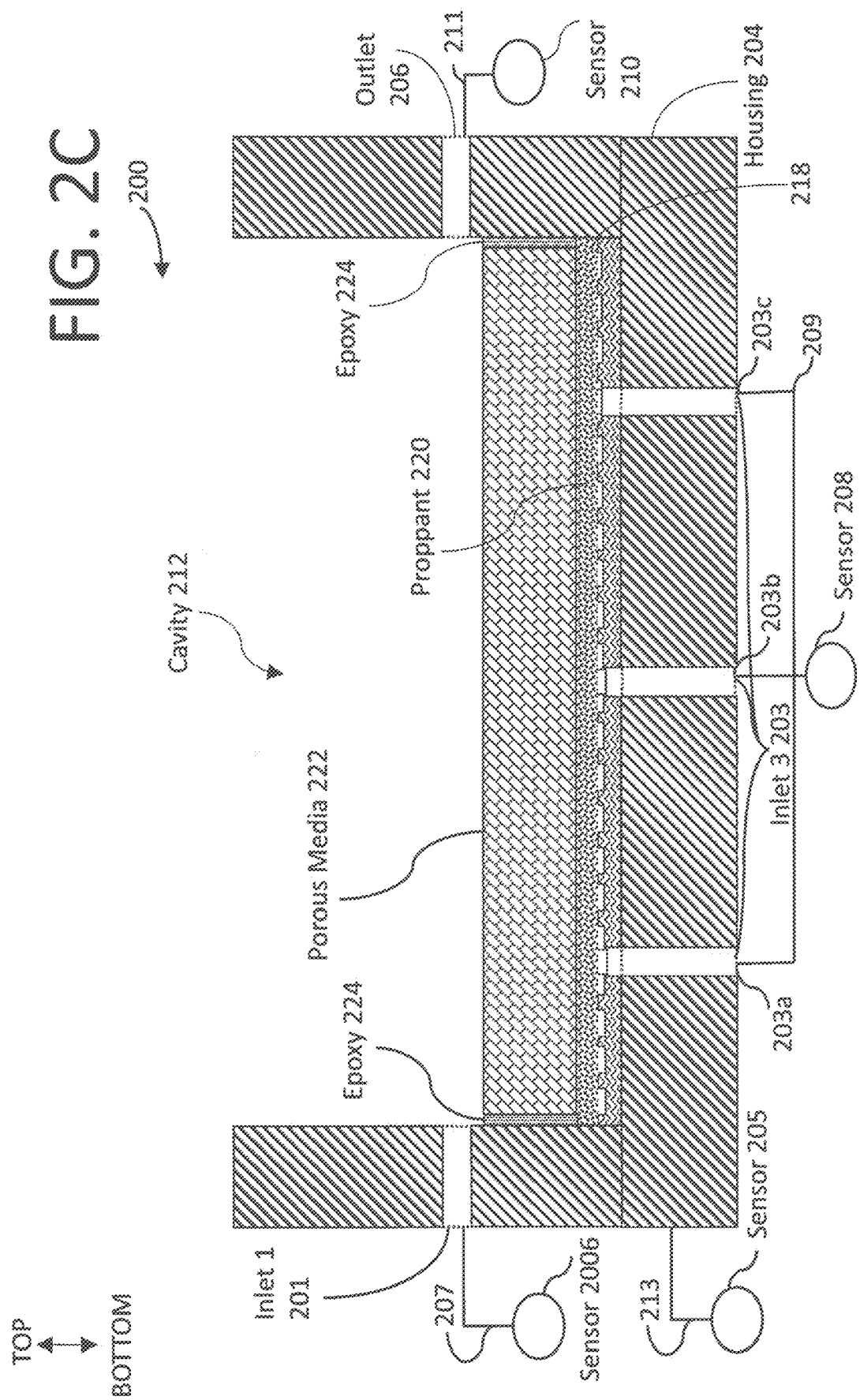

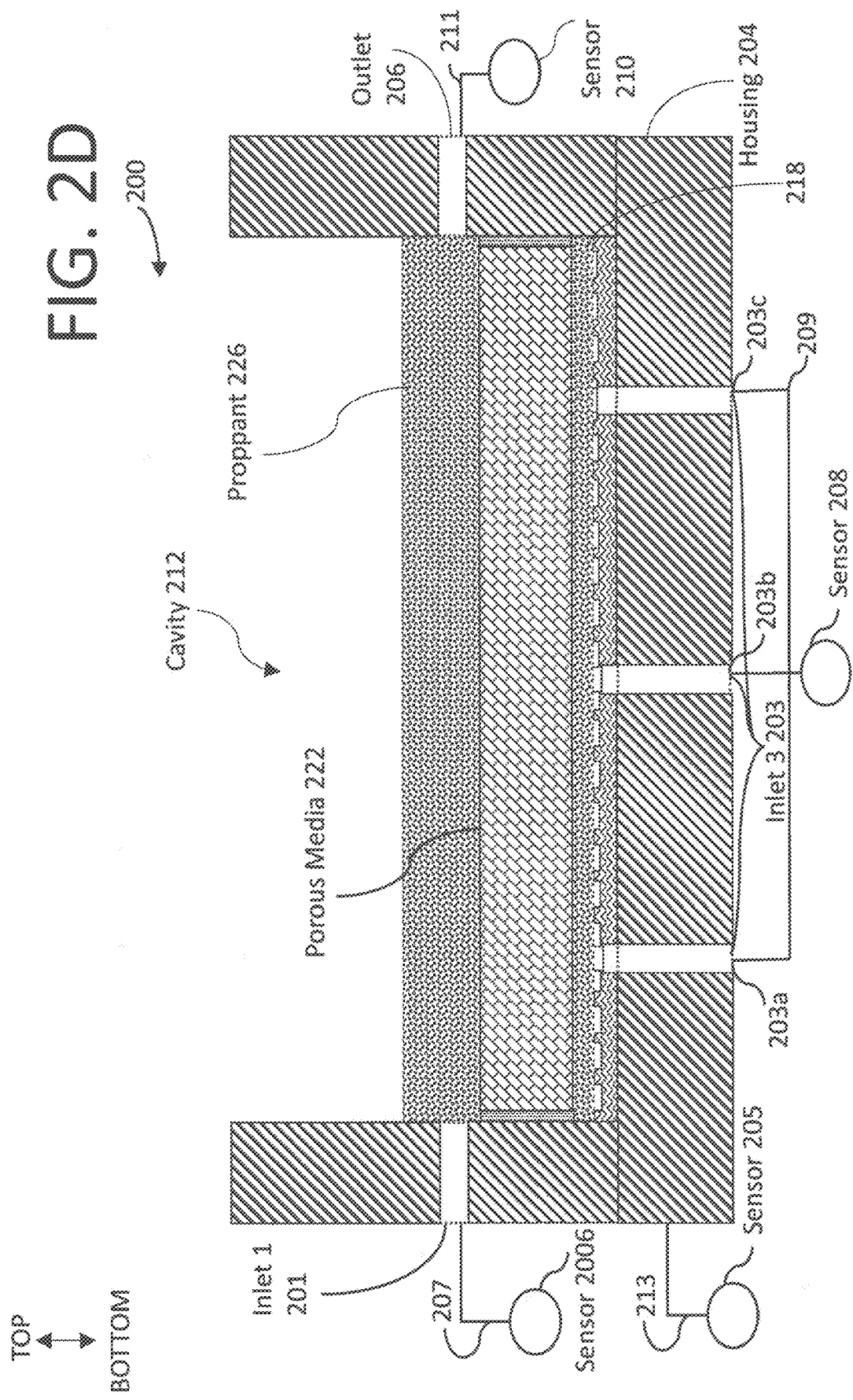

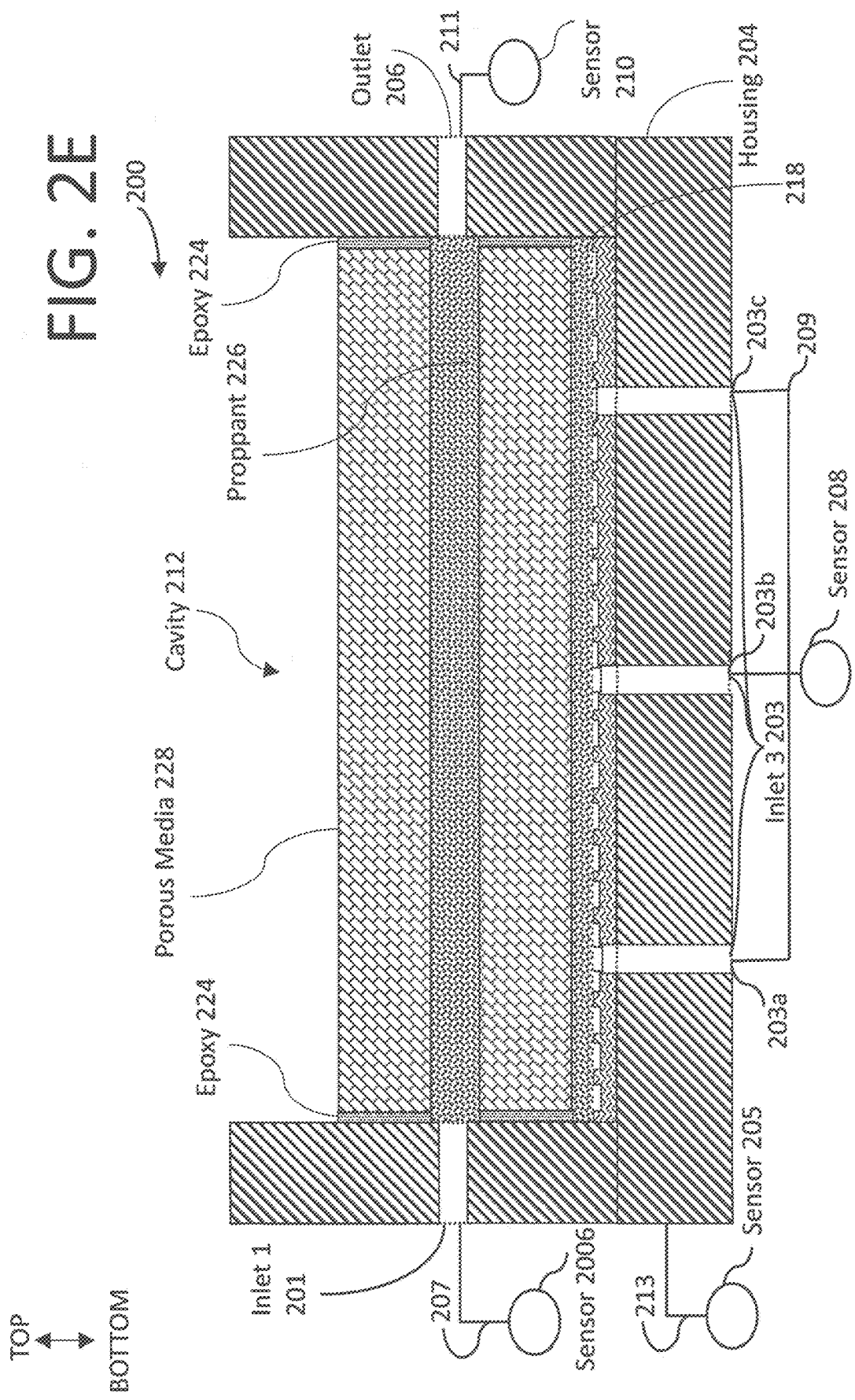

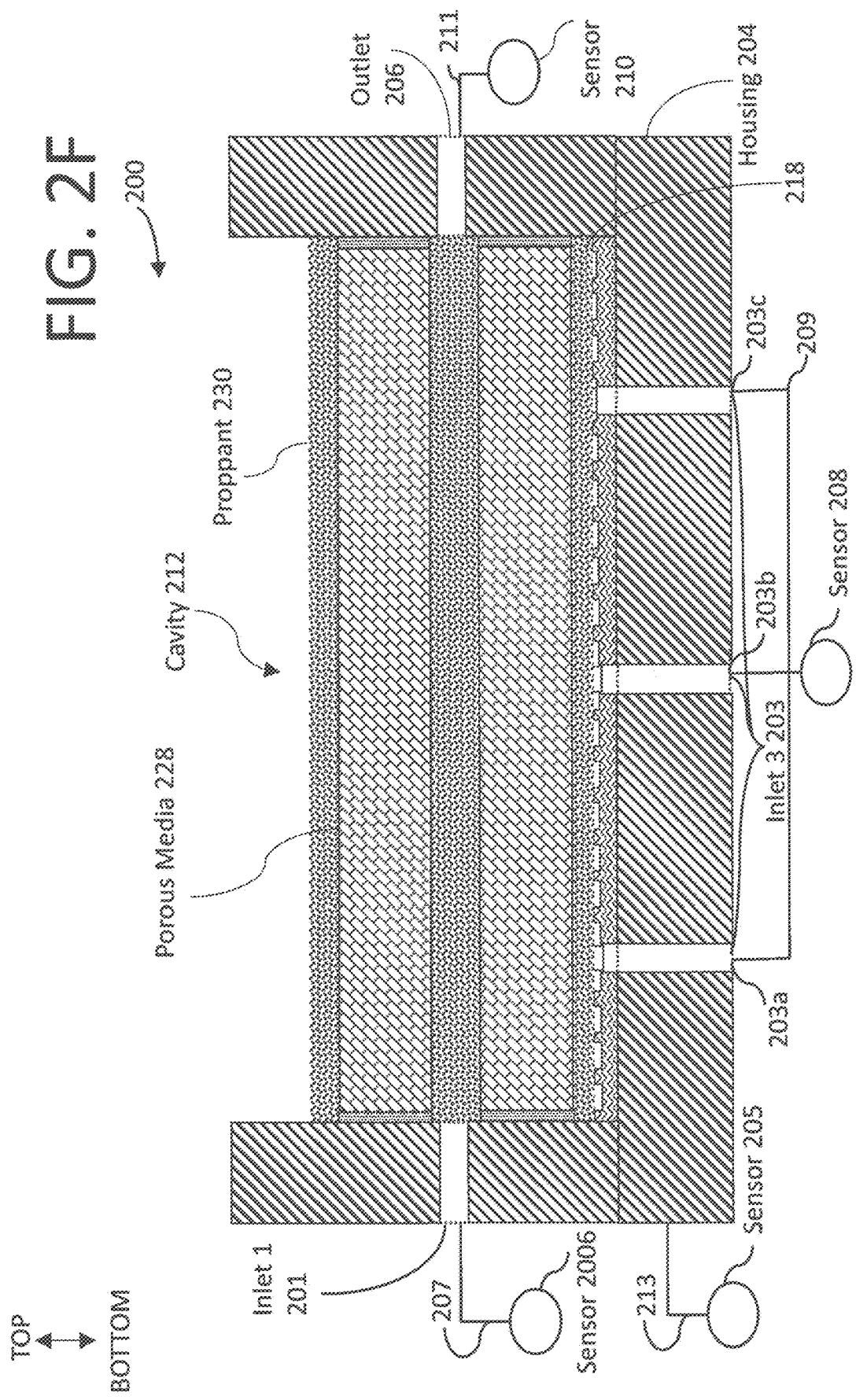

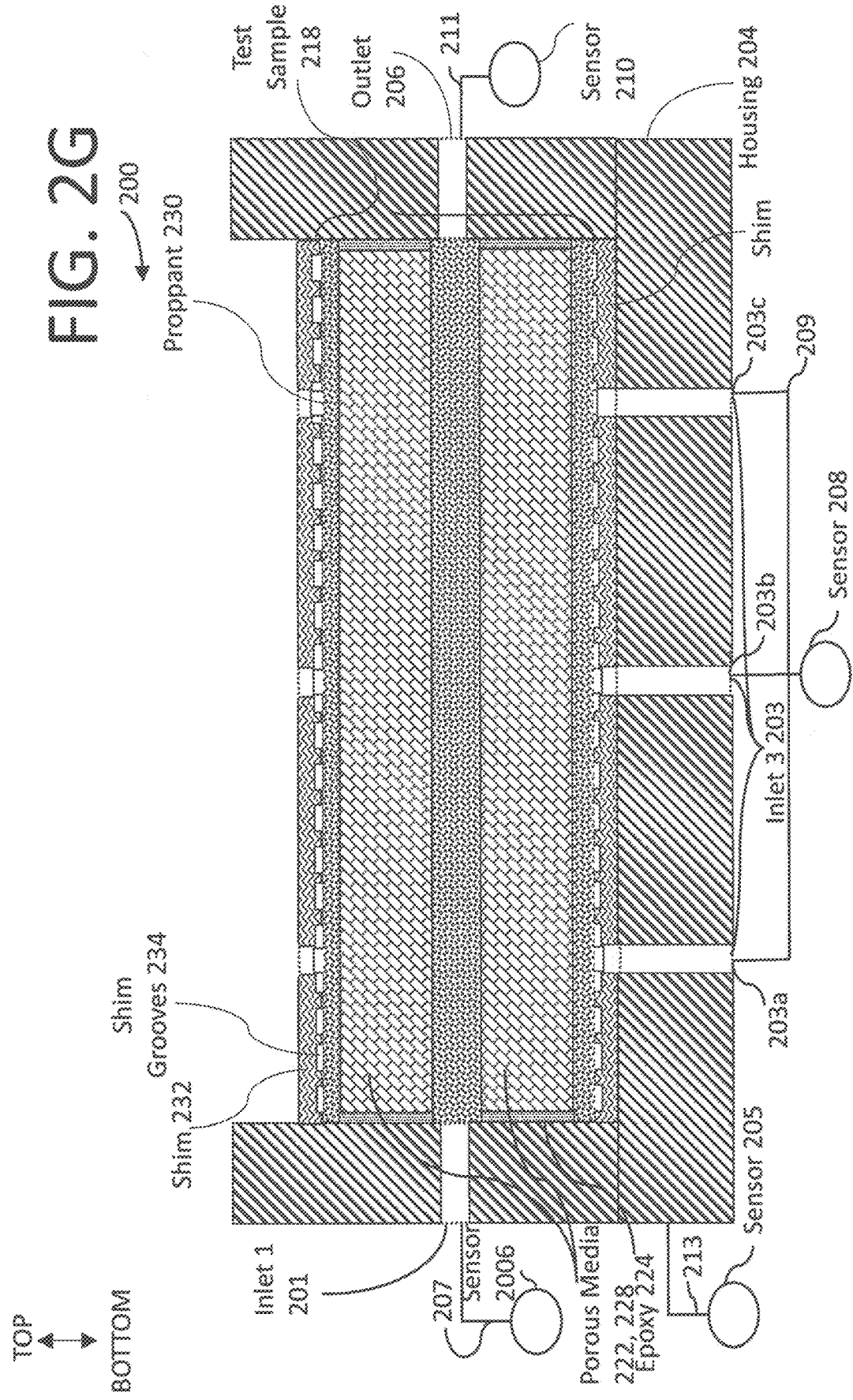

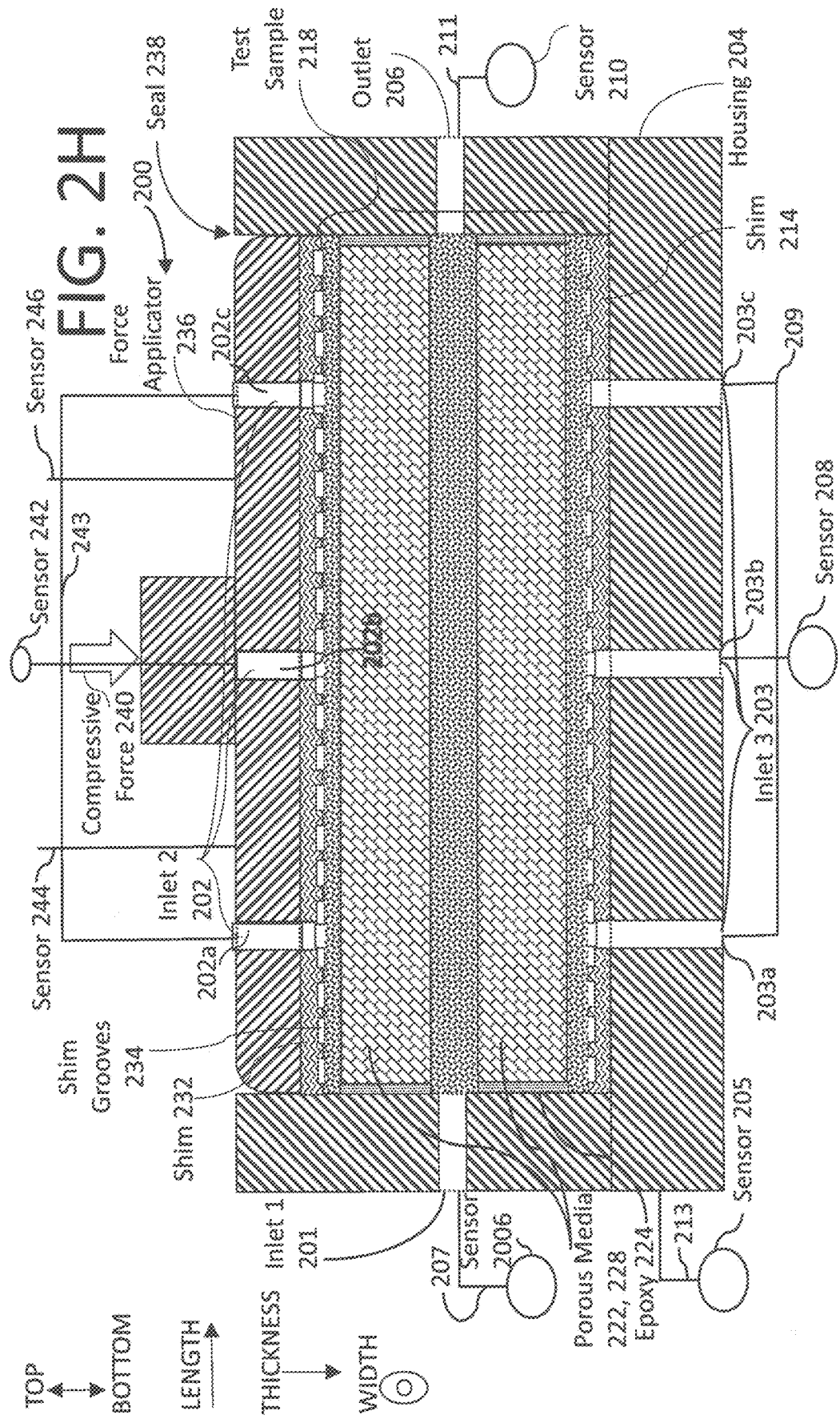

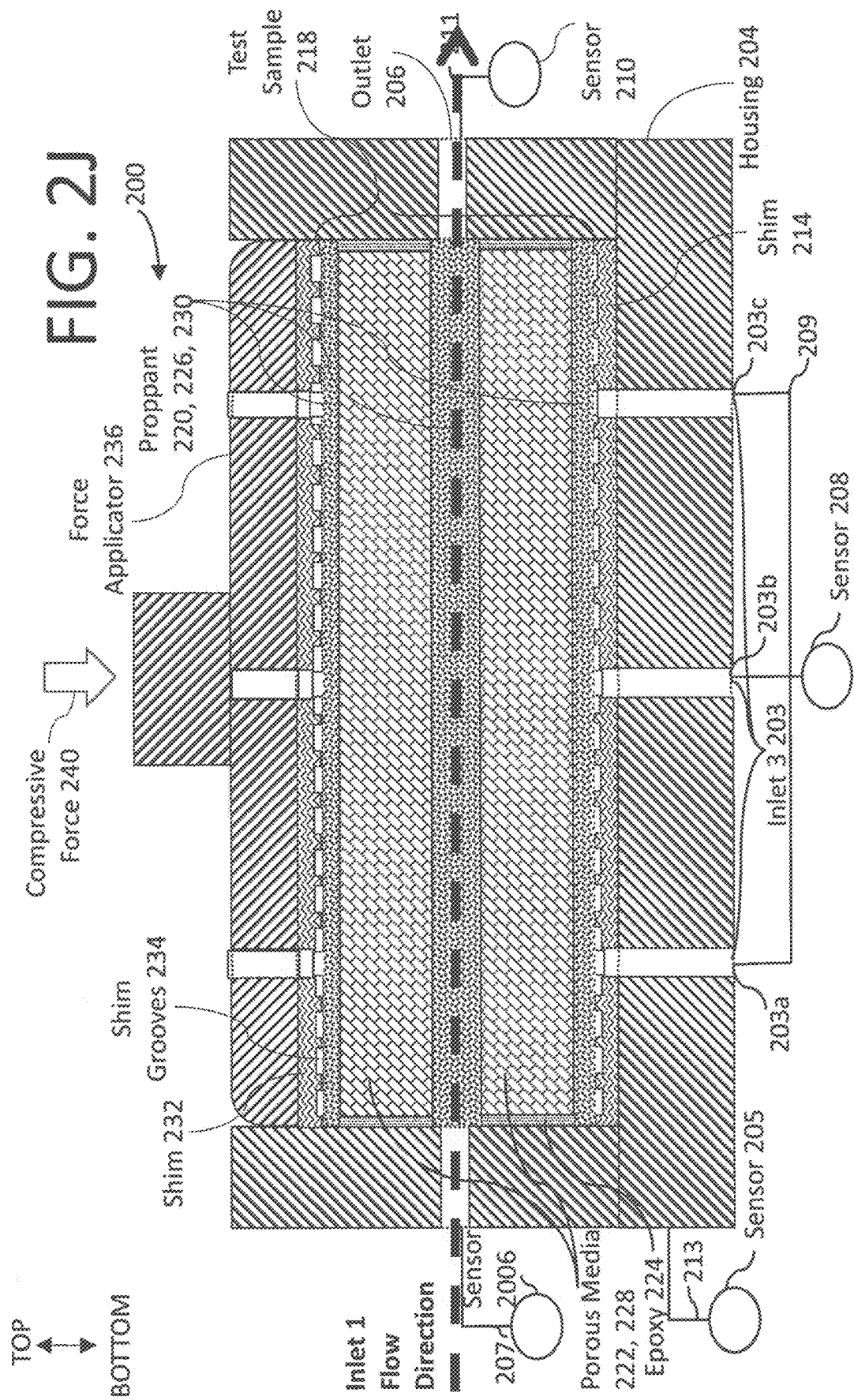

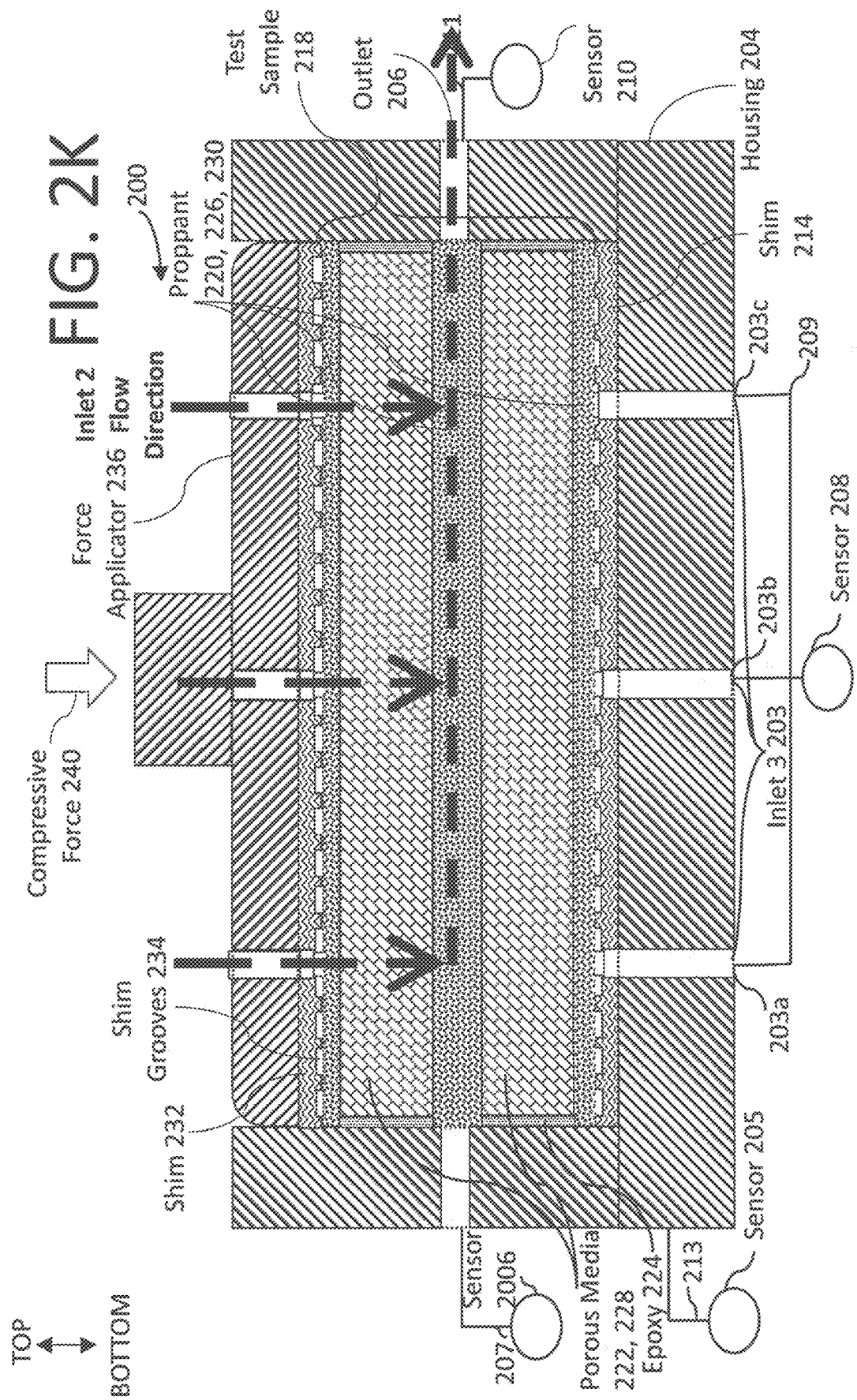

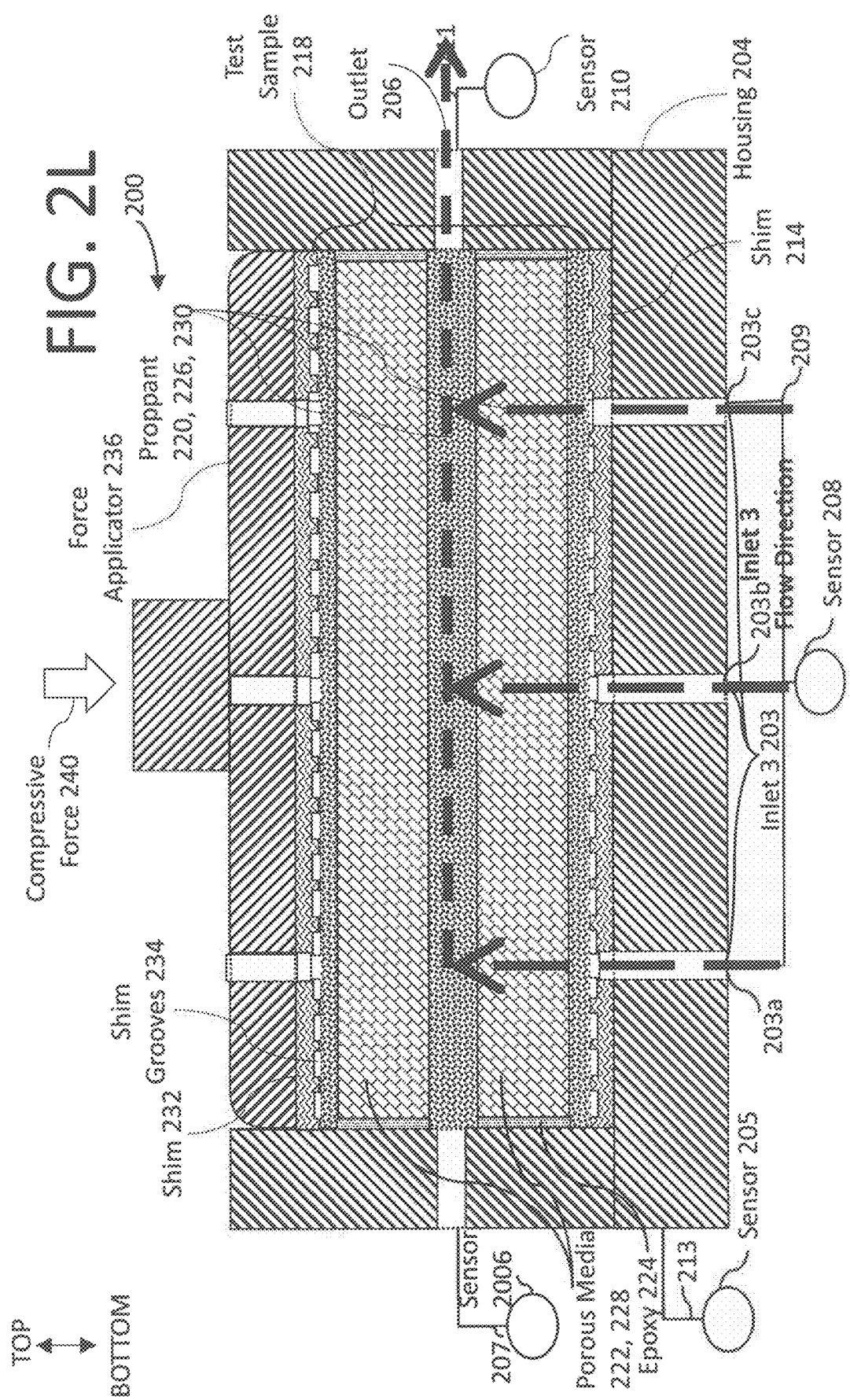

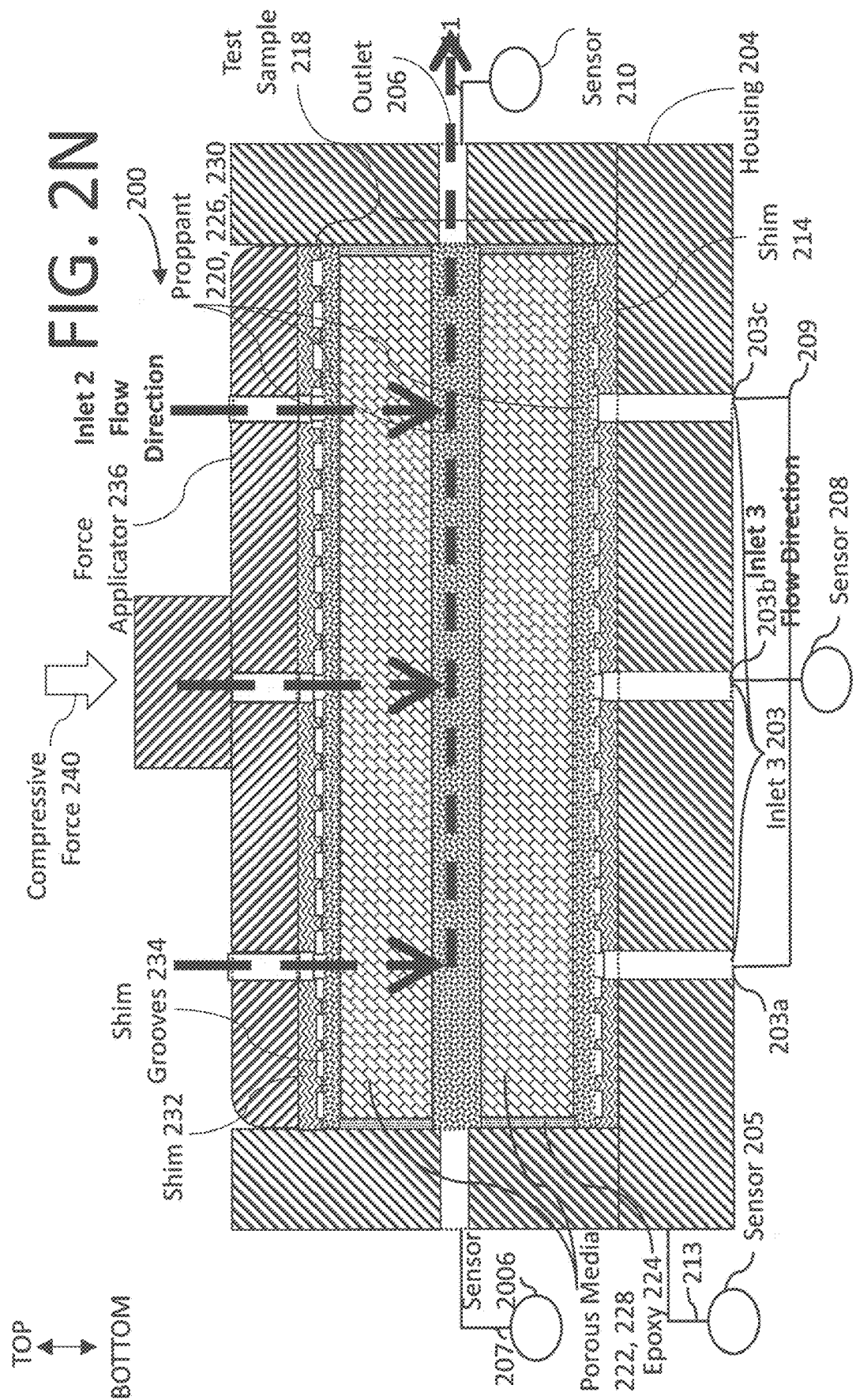

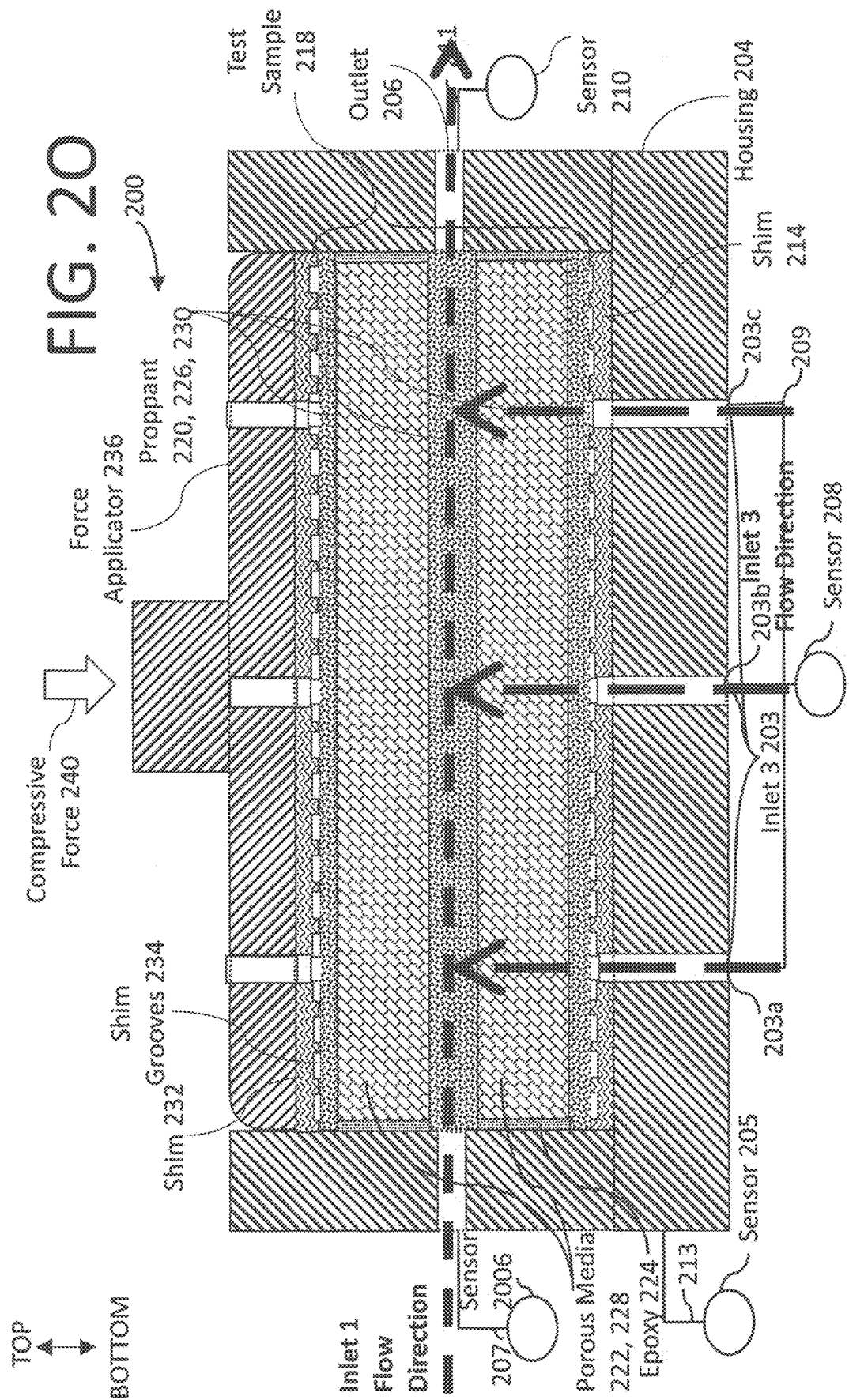

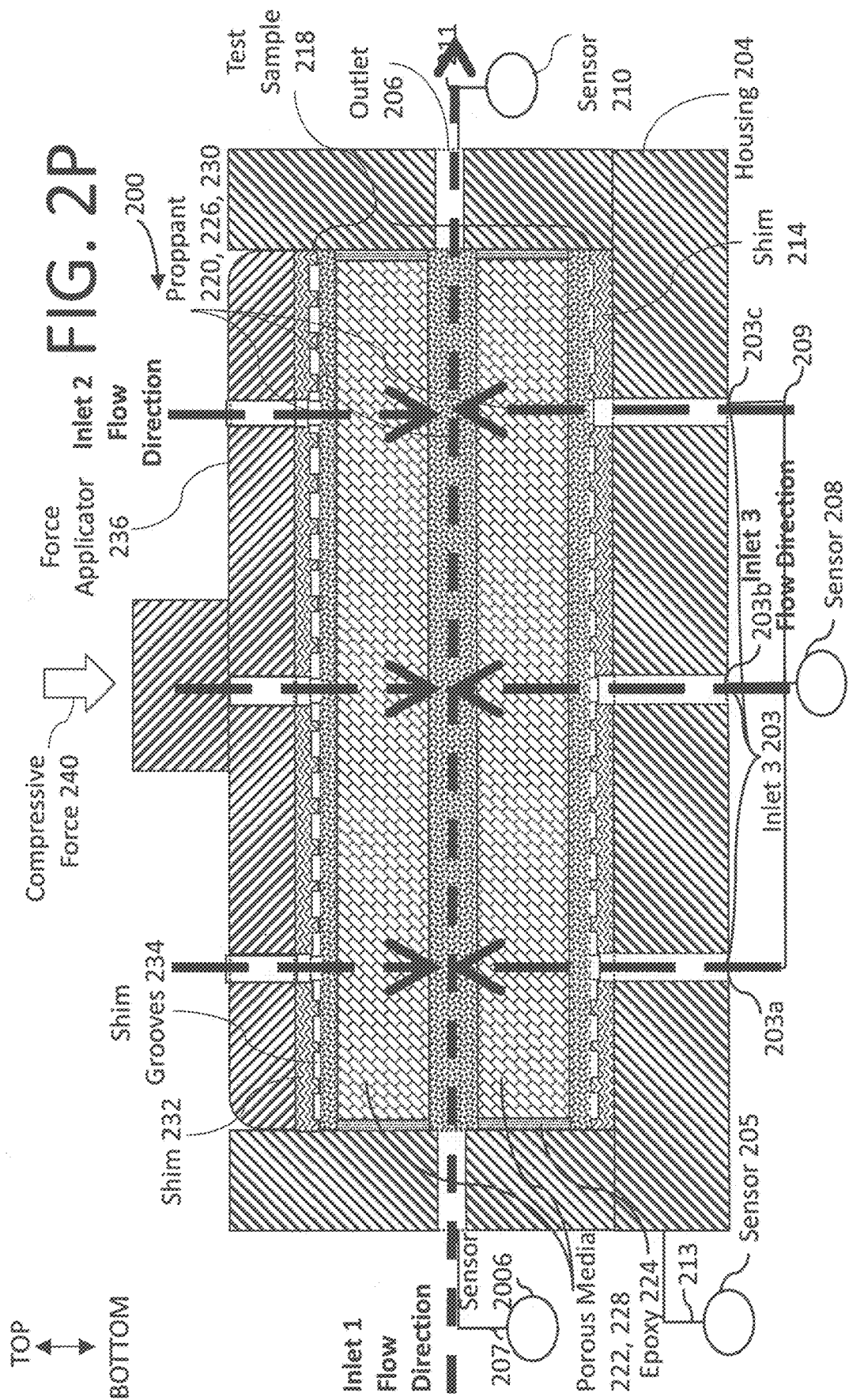

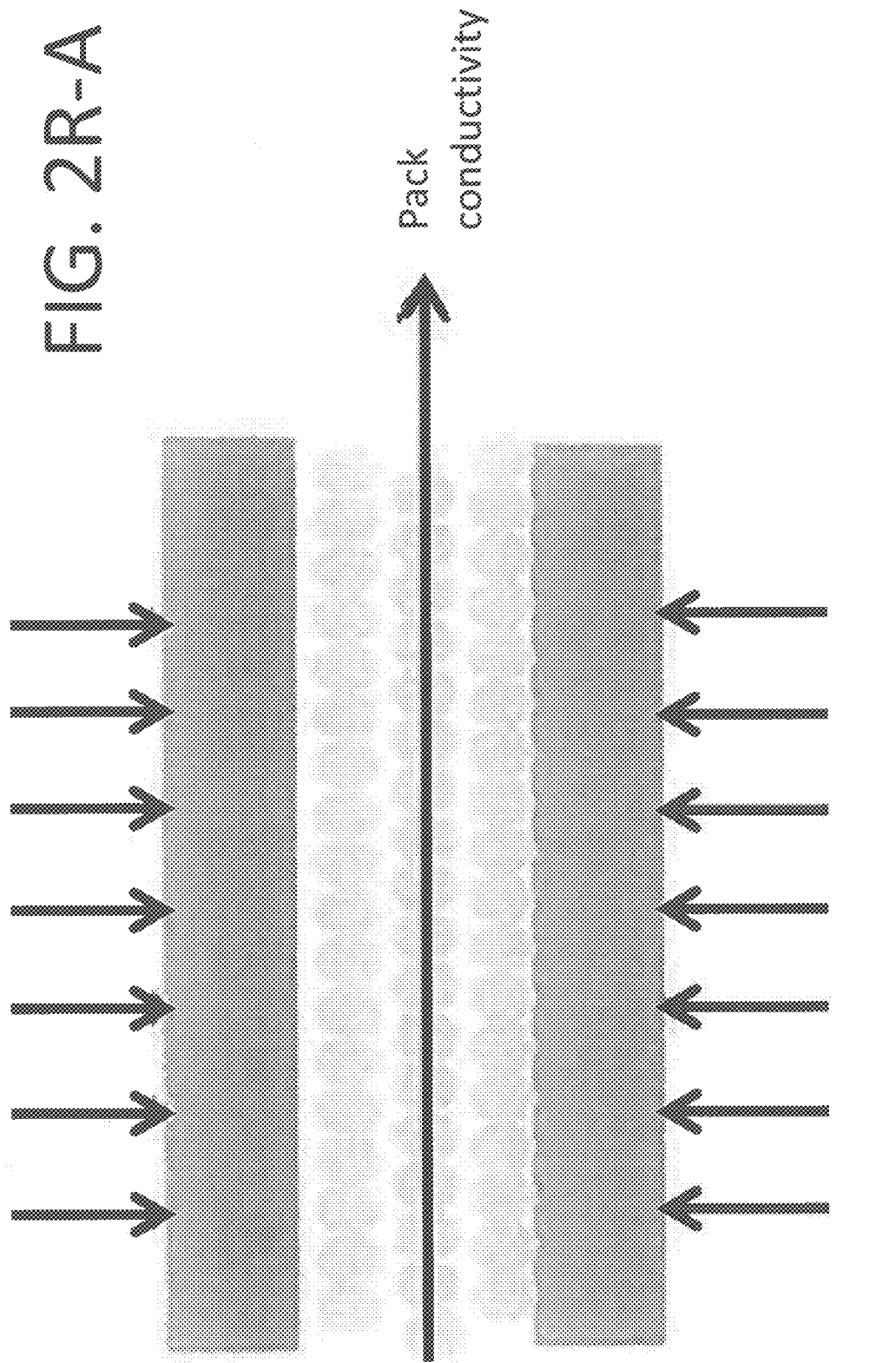

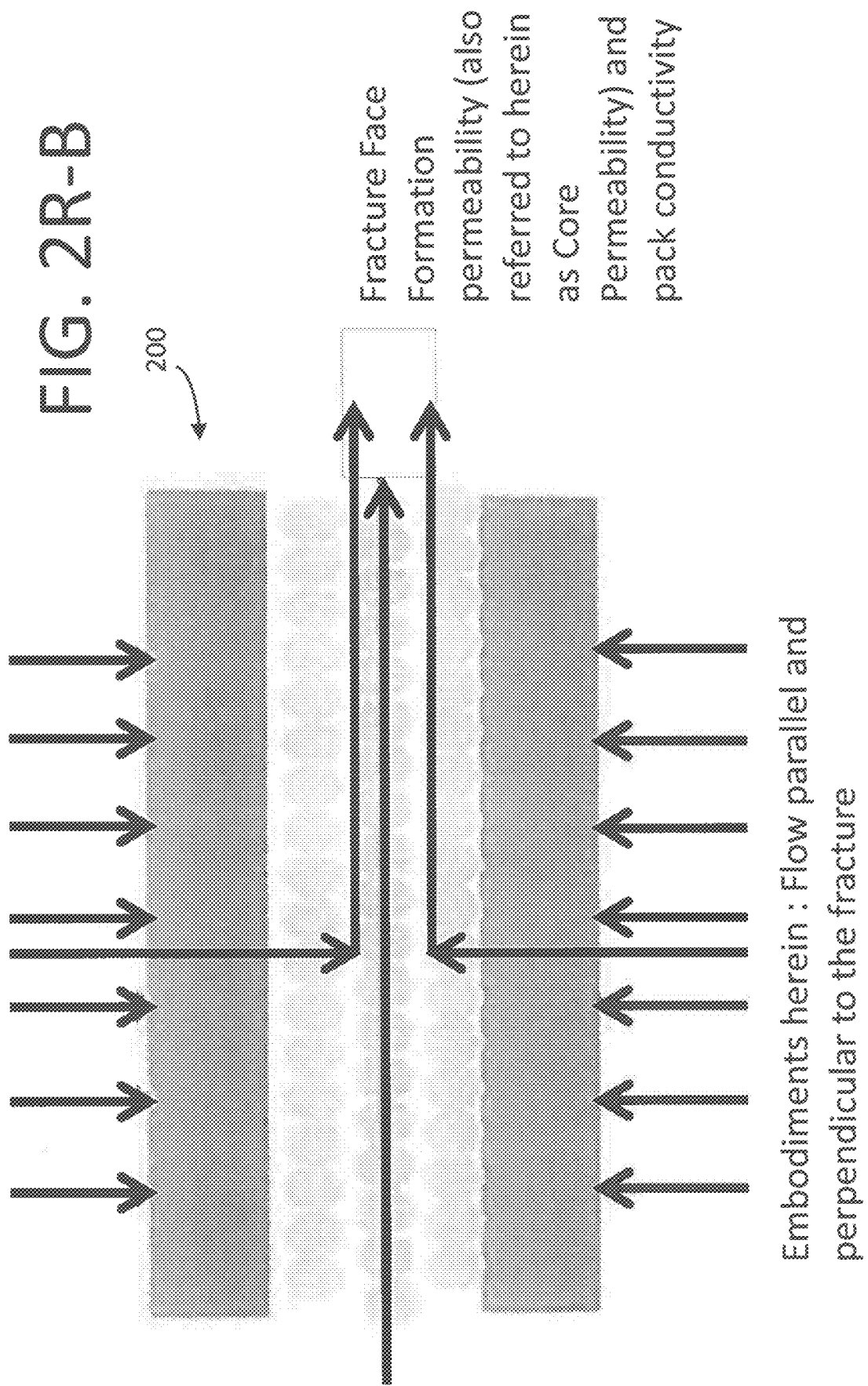
FIG. 2R-B

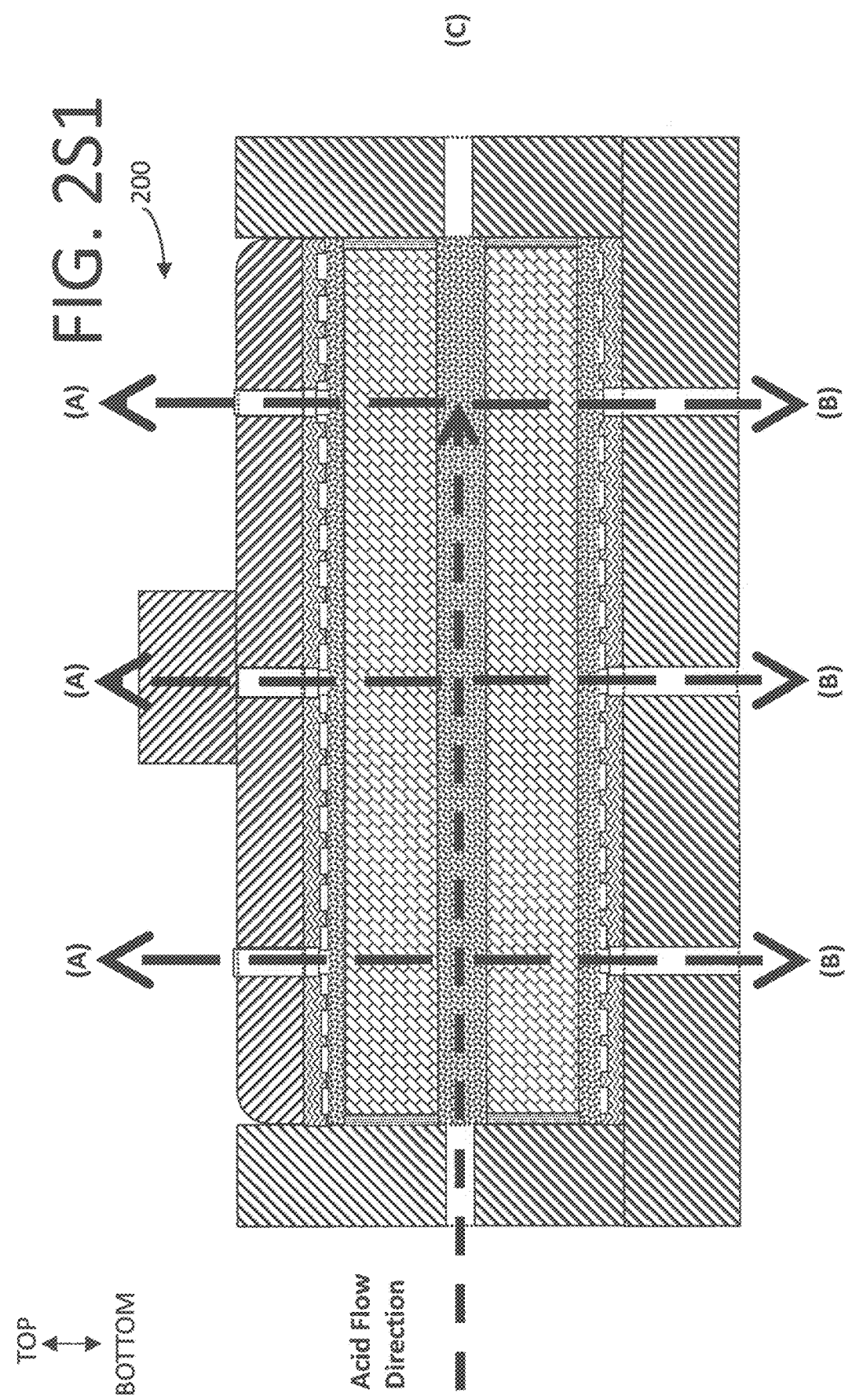

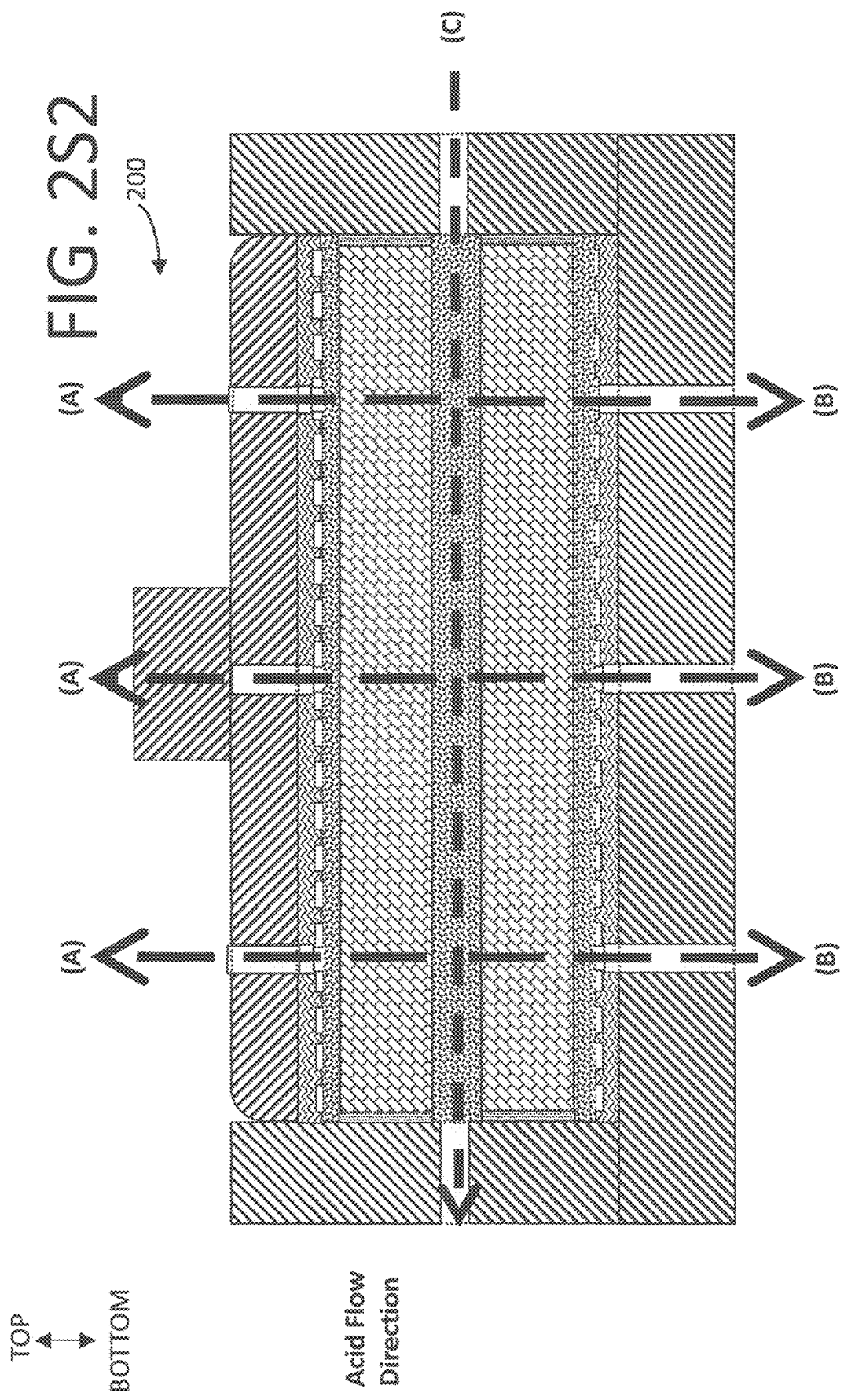
FIG. 2S2

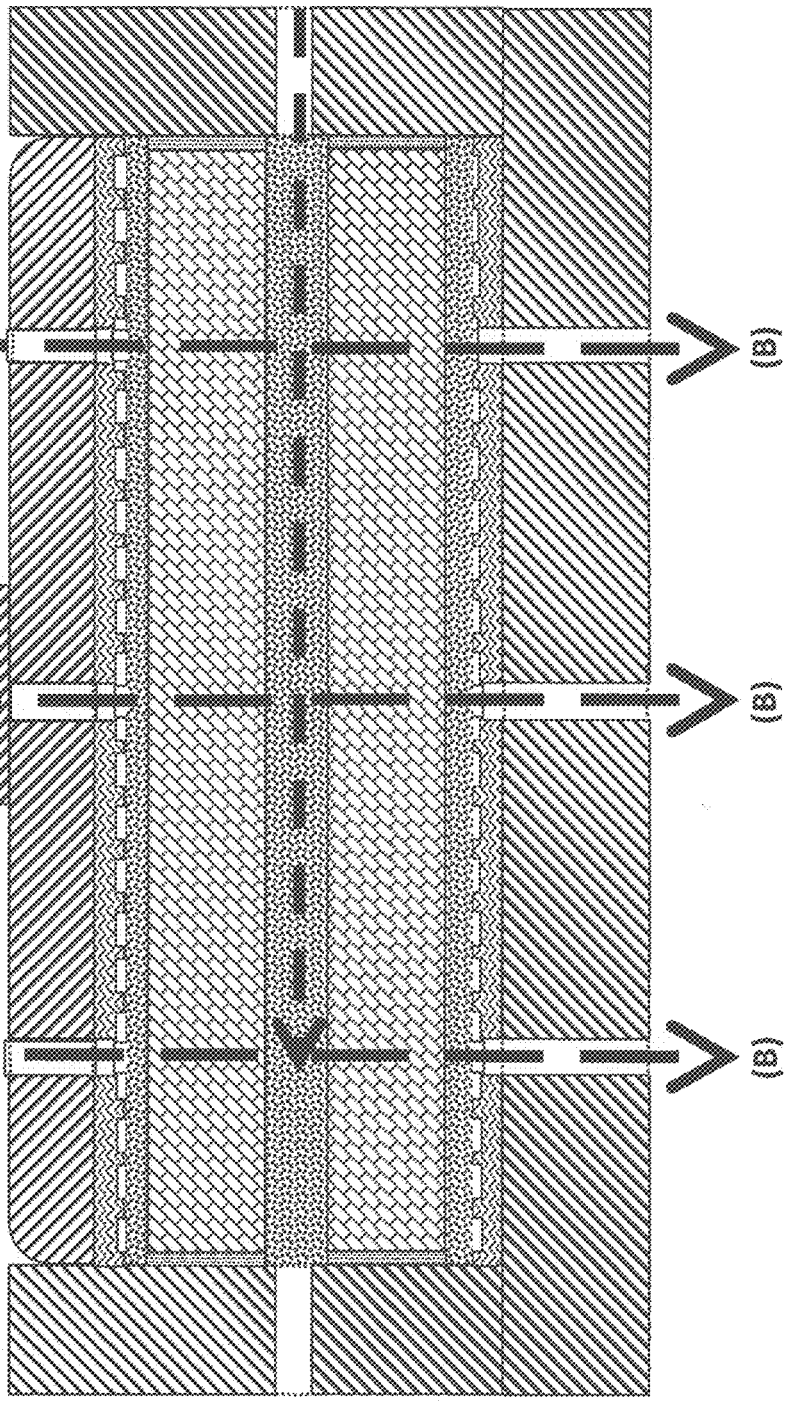

SYSTEMS AND METHODS FOR FRACTURE FACE FORMATION PERMEABILITY MEASUREMENTS

CROSS REFERENCES TO RELATED APPLICATIONS

This application claims benefit under 35 USC 119 of U.S. Provisional Patent App. No. 62/689,617 with a filing date of Jun. 25, 2018, which is incorporated by reference in its entirety and for all purposes.

STATEMENT REGARDING FEDERALLY SPONSORED RESEARCH OR DEVELOPMENT

Not applicable.

TECHNICAL FIELD

The disclosed embodiments relate generally to fracturing, and in particular, the disclosed embodiments relate to analyzing test samples in the area of fracturing.

BACKGROUND

Hydraulic fracturing is used in oil and gas wells to increase oil production from the low permeability reservoir zones. In addition, hydraulic fracturing is used to improve wellbore-reservoir communication by bypassing near wellbore damage (e.g., reduced permeability) and minimizing fines migration tendency from those zones. Propped fracturing helps keep the fractures open for extended periods of time, allowing good conductivity and transport of hydrocarbons to the wellbore region. However, there are many factors that work against achieving sustained production rates from propped fractures under depletion conditions. Those are: (a) Fines migration (b) Proppant embedment and fracture aperture reduction; and (c) Proppant crushing and proppant diagenesis. In addition to resulting in reduced fracture aperture and reduced fracture conductivity, proppant embedment at the fracture face (also referred to as frac face) can result in reduced hydrocarbon flow from the matrix into the fracture due to reduced pore throat size, crushing of the rock, accelerated fines generation, and pore plugging within the embedment zone.

Proppant conductivity tests are conducted to estimate reduction in a propped fracture's conductivity as a function of stress. In these tests, the proppant is sandwiched between two platens composed of quarried core or formation material. The proppant is typically loaded at 21 bm/ft2 and the test performed with 2% KCl. Temperatures range from 150° F.-250° F. and each stress step lasts 50 hours.

There is a limitation to the current proppant conductivity test practices (e.g., API RP19C Measurement of Properties of Proppants Used in Hydraulic Fracturing and Gravel-packing Operations) when the overall contribution of proppant embedment on production rate decline from a fracture is being studied: Current proppant conductivity tests typically only measure conductivity losses that can occur within the high permeability proppant pack. The source of the conductivity loss addressed by those tests is frac gel damage and reduction in fracture aperture due to stress. The damage at the fracture face cannot be assessed.

There exists a need for improved manner of analyzing test samples in the area of fracturing.

SUMMARY

In one aspect, provided herein is an embodiment of a system, the system comprises a housing having a cavity defined therein for holding a test sample; a first inlet in fluid communication with the cavity to deliver fluid to the test sample; a second inlet in fluid communication with the cavity to deliver fluid to the test sample, the first inlet configured to deliver fluid to the test sample in a direction substantially perpendicular to a direction that the second inlet is configured to deliver fluid to the test sample; an outlet in fluid communication with the cavity to receive fluid from the test sample; and a force applicator configured to apply compressive force to the test sample within the cavity. The force applicator forms a seal with the housing while applying compressive force to the test sample. The system further comprises at least one sensor configured to, while fluid flows from at least one of the inlets through the test sample to the outlet, determine a fluid characteristic, a test sample characteristic, or any combination thereof.

In one aspect, provided herein is an embodiment of a method, the method comprises flowing fluid through a test sample using a first fluid inlet and a fluid outlet; flowing fluid through the test sample using another fluid inlet and the fluid outlet, wherein the first inlet is configured to deliver fluid to the test sample in a direction perpendicular to a direction that the other fluid inlet is configured to deliver fluid to the test sample; applying a compressive force to the test sample while fluid flows through the test sample; and while fluid flows from at least one of the inlets through the test sample to the fluid outlet, determining a fluid characteristic, a test sample characteristic, or any combination thereof.

DESCRIPTION OF THE DRAWINGS

FIG. 1C illustrates one embodiment of a computing system that may be utilized with the test analysis system of FIG. 1A.

FIGS. 2A-2Q and 2R-B illustrate embodiments of a test sample analysis system.

FIG. 2R-A illustrates a comparison between FIG. 2R-B.

FIGS. 2S1, 2S2, and 2S3 illustrate some embodiments of the test sample analysis system flowing fluid comprising acid.

FIG. 3 illustrate a flowchart of one embodiment of a method of analyzing a test sample.

Figure 1A:
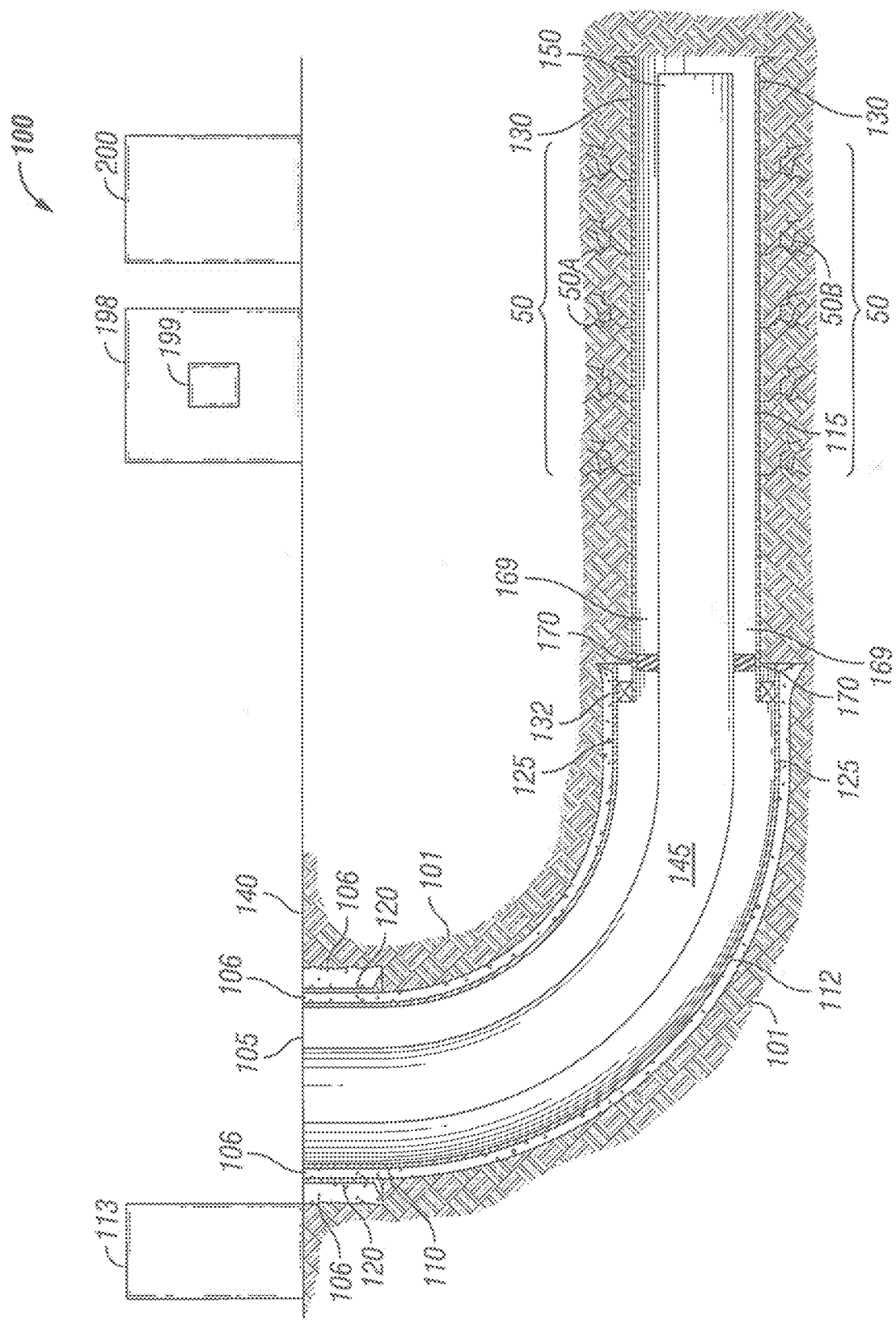
FIG. 1A illustrates an expanded view, in cross-section, of one embodiment of a hydrocarbon exploration and hydrocarbon recovery system, including one embodiment of a test analysis system in accordance with the instant disclosure.

Reference will now be made in detail to various embodiments, where like reference numerals designate corresponding parts throughout the several views. In the following detailed description, numerous specific details are set forth in order to provide a thorough understanding of the present disclosure and the embodiments described herein. However, embodiments described herein may be practiced without these specific details. In other instances, well-known methods, procedures, components, and mechanical apparatus have not been described in detail so as not to unnecessarily obscure aspects of the embodiments.

DETAILED DESCRIPTION

TERMINOLOGY: The following terms will be used throughout the specification and will have the following meanings unless otherwise indicated.

Hydrocarbon exploration processes, hydrocarbon recovery processes, or any combination thereof may be performed on a "subsurface volume of interest" (also referred to as a "formation"). The "subsurface volume of interest" refers to practically anything under a surface. For example, the subsurface volume of interest may be practically anything under a terrestrial surface (e.g., practically anything under a land surface), practically anything under a seafloor, etc. A water column may be above the subsurface volume of interest, for example, in marine hydrocarbon exploration, in marine hydrocarbon recovery, etc. The subsurface volume of interest may be onshore in some embodiments. Alternatively, the subsurface volume of interest may be offshore, with shallow water or deep water above the subsurface volume of interest, in some embodiments. The subsurface volume of interest may include faults, fractures, overburdens, underburdens, salts, salt welds, rocks, sands, sediments, pore space, etc. The subsurface volume of interest may include practically any geologic point(s) or volume(s) of interest (such as a survey area).

The subsurface volume of interest may also include hydrocarbons, such as liquid hydrocarbons (also known as oil or petroleum), gas hydrocarbons (e.g., natural gas), solid hydrocarbons (e.g., asphaltenes or waxes), a combination of hydrocarbons (e.g., a combination of liquid hydrocarbons, gas hydrocarbons, and solid hydrocarbons), etc. Light crude oil, medium oil, heavy crude oil, and extra heavy oil, as defined by the American Petroleum Institute (API) gravity, are examples of hydrocarbons. Indeed, examples of hydrocarbons are many, and may include, oil, natural gas, kerogen, bitumen, clathrates (also referred to as hydrates), etc. The subsurface volume of interest may be known to include hydrocarbons in some embodiments. However, the subsurface volume of interest may not be known to include hydrocarbons, such as during hydrocarbon exploration, in other embodiments.

The subsurface volume of interest may also include at least one wellbore. For example, at least one wellbore may be drilled into the subsurface volume of interest in order to confirm the presence of hydrocarbons. As another example, at least one preexisting wellbore into the subsurface volume of interest or at least one new wellbore drilled into the subsurface may be used to recover the hydrocarbons. The hydrocarbons may be recovered from the entire subsurface or from a portion of the subsurface. For example, the subsurface may be divided up into one or more hydrocarbon zones, and hydrocarbons may be recovered from each desired hydrocarbon zone. In some embodiments, one or more of hydrocarbon zones may even be shut in to increase hydrocarbon recovery from a hydrocarbon zone that is not shut in.

The hydrocarbons may be recovered (sometimes referred to as produced) from the subsurface volume of interest using primary recovery (e.g., by relying on pressure to recover the hydrocarbons), secondary recovery (e.g., by using water injection (also referred to as waterflooding) or natural gas injection to recover hydrocarbons), enhanced oil recovery (EOR), or any combination thereof. The term "enhanced oil recovery" refers to techniques for increasing the amount of hydrocarbons that may be extracted from the subsurface volume of interest. Enhanced oil recovery may also be referred to as improved oil recovery or tertiary oil recovery. Secondary recovery may also just be referred to as enhanced oil recovery. Other methodologies known by those of ordinary skill in the art may also be utilized to recover the hydrocarbons.

EOR processes include, for example: (a) miscible gas injection (which includes, for example, carbon dioxide flooding), (b) chemical injection (sometimes referred to as chemical enhanced oil recovery (CEOR), and which includes, for example, polymer flooding, alkaline flooding, surfactant flooding, conformance control, as well as combinations thereof such as alkaline-polymer flooding, surfactant-polymer flooding, or alkaline-surfactant-polymer flooding), (c) microbial injection, (d) thermal recovery (which includes, for example, cyclic steam and steam flooding), or any combination thereof.

The hydrocarbons may also be recovered from the subsurface volume of interest using fracturing. For example, fracturing may include fracturing using electrodes, fracturing using fluid (oftentimes referred to as hydraulic fracturing), etc. For example, hydraulic fracturing may entail preparing an injection fluid (oftentimes referred to a fracturing fluid) and injecting that fracturing fluid into the wellbore at a sufficient rate and pressure to open existing fractures and/or create fractures in the subsurface volume of interest. The fractures permit hydrocarbons to flow more freely into the wellbore.

In the hydraulic fracturing process, the fracturing fluid may be prepared on-site to include at least proppants. The proppants, such as sand or other particles, are meant to hold the fractures open so that hydrocarbons can more easily flow to the wellbore. The fracturing fluid and the proppants may be blended together using at least one blender. The fracturing fluid may also include other components in addition to the proppants. The wellbore and the subsurface volume of interest proximate to the wellbore are in fluid communication (e.g., via perforations), and the fracturing fluid with the proppants is injected into the wellbore through a wellhead of the wellbore using at least one pump (oftentimes called a fracturing pump). The fracturing fluid with the proppants is injected at a sufficient rate and pressure to open existing fractures and/or create fractures in the subsurface volume of interest. As fractures become sufficiently wide to allow proppants to flow into those fractures, proppants in the fracturing fluid are deposited in those fractures during injection of the fracturing fluid. After the hydraulic fracturing process is completed, the fracturing fluid is removed by flowing or pumping it back out of the wellbore so that the fracturing fluid does not block the flow of hydrocarbons to the wellbore. The hydrocarbons will typically enter the same wellbore from the subsurface volume of interest and go up to the surface for further processing.

The equipment to be used in preparing and injecting the fracturing fluid may be dependent on the components of the fracturing fluid, the proppants, the wellbore, the subsurface volume of interest, etc. However, for simplicity, the term "fracturing apparatus" is meant to represent any tank(s), mixer(s), blender(s), pump(s), manifold(s), line(s), valve(s), fluid(s), fracturing fluid component(s), proppants, and other equipment and non-equipment items related to preparing the fracturing fluid and injecting the fracturing fluid. Those of ordinary will also appreciate that there may be some overlap between the "fracturing apparatus" and the "injection apparatus," such that some items (e.g., a tank, a mixer, etc.) may be used in multiple processes.

The hydrocarbons may also be recovered from the subsurface volume of interest using radio frequency (RF) heating. For example, at least one radio frequency antenna may be utilized to increase the temperature of hydrocarbons, such as heavy oil, to reduce viscosity. The hydrocarbons with lower viscosity may then be produced from the subsurface volume of interest with an improved flow rate.

The physical equipment to be used in radio frequency heating is dependent on the wellbore, the subsurface volume of interest, etc. However, for simplicity, the term "radio frequency heating apparatus" is meant to represent any antenna(s), fluid(s), and other equipment and non-equipment items related to radio frequency heating.

Other hydrocarbon recovery processes may also be utilized to recover the hydrocarbons. Furthermore, those of ordinary skill in the art will appreciate that one hydrocarbon recovery process may also be used in combination with at least one other recovery process. For example, radio frequency heating may be used in combination with at least one other recovery process, such as, but not limited to, steam flooding.

The subsurface volume of interest, the hydrocarbons, or any combination thereof may also include non-hydrocarbon items. For example, non-hydrocarbon items may include connate water, brine, tracers, items used in enhanced oil recovery or other hydrocarbon recovery processes, items from other types of treatments (e.g., gels used in conformance control), etc.

In short, each subsurface volume of interest may have a variety of characteristics, such as petrophysical rock properties, reservoir fluid properties, reservoir conditions, or any combination thereof. For example, each subsurface volume of interest may be associated with one or more of: temperature, porosity, permeability, water composition, mineralogy, hydrocarbon type, hydrocarbon quantity, reservoir location, pressure, etc. Indeed, those of ordinary skill in the art will appreciate that the characteristics are many, including, but not limited to: shale gas, shale oil, tight gas, tight oil, tight carbonate, carbonate, vuggy carbonate, unconventional (e.g., a rock matrix with an average pore size less than 1 micrometer), diatomite, geothermal, coalbed methane, a methane hydrate containing subsurface volume of interest, a mineral containing subsurface volume of interest, a metal containing subsurface volume of interest, a subsurface volume of interest having a permeability in the range of 0.01 microdarcy to 10 millidarcy, a subsurface volume of interest having a permeability in the range of 10 millidarcy to 40,000 millidarcy, etc.

The term "subsurface volume of interest" may be used synonymously with the term "reservoir" or "subsurface reservoir" or "subsurface region of interest" or "formation" or "subsurface formation." The subsurface volume of interest may also include a reservoir, a formation, or any combination thereof. Thus, the terms "subsurface volume of interest," "hydrocarbons," and the like are not limited to any description or configuration described herein.

"Wellbore" refers to a single hole, usually cylindrical, that is drilled into the subsurface volume of interest for hydrocarbon exploration, hydrocarbon recovery, or any combination thereof. The wellbore is surrounded by the subsurface volume of interest and the wellbore may be in fluidic communication with the subsurface volume of interest (e.g., via perforations). The wellbore may also be in fluidic communication with the surface, such as a surface facility that may include oil/gas/water separators, gas compressors, storage tanks, pumps, gauges, pipelines, etc.

The wellbore may be used for injection in some embodiments. The wellbore may be used for production in some embodiments. The wellbore may be used for fracturing in some embodiments. The wellbore may be used for a single function, such as only injection, in some embodiments. The wellbore may be used for a plurality of functions, such as both injection and production in some embodiments. The use of the wellbore may also be changed, for example, a particular wellbore may be turned into an injection wellbore after a different previous use. The wellbore may be drilled amongst existing wellbores as an infill wellbore. A plurality of wellbores (e.g., tens to hundreds of wellbores) are often used in a field to recover hydrocarbons. As an example, the hydrocarbons may be swept from a single injection wellbore towards at least one production wellbore and then up towards the surface for further processing.

The wellbore may have vertical, horizontal, or combination trajectories. For example, the wellbore may be a vertical wellbore, a horizontal wellbore, a multilateral wellbore, an inclined wellbore, a slanted wellbore, etc. The wellbore may include a "build section." "Build section" refers to practically any section of a wellbore where the deviation is changing. As an example, the deviation is changing when the wellbore is curving. In a horizontal wellbore, the build section is the curved section between the vertical section of the horizontal wellbore and the horizontal section of the horizontal wellbore. Wellbores that are not horizontal wellbores may also include build sections. For example, inclined or slanted wellbores may each include a build section.

The wellbore may include a plurality of components, such as, but not limited to, a casing, a liner, a tubing string, a heating element, a sensor, a packer, a screen, a gravel pack, artificial lift equipment (e.g., an electric submersible pump (ESP)), etc. The "casing" refers to a steel pipe cemented in place during the wellbore construction process to stabilize the wellbore. The "liner" refers to any string of casing in which the top does not extend to the surface but instead is suspended from inside the previous casing. The "tubing string" or simply "tubing" is made up of a plurality of tubulars (e.g., tubing, tubing joints, pup joints, etc.) connected together. The tubing string is lowered into the casing or the liner for injecting a fluid into the subsurface volume of interest, producing a fluid from the subsurface volume of interest, or any combination thereof. The casing may be cemented in place, with the cement positioned in the annulus between the subsurface volume of interest and the outside of the casing. The wellbore may also include any completion hardware that is not discussed separately. If the wellbore is drilled offshore, for example, the wellbore may include some of the previous components plus other components such as a riser, etc.

The wellbore may also include equipment to control fluid flow into the wellbore, control fluid flow out of the wellbore, or any combination thereof. For example, each wellbore may include a wellhead, a BOP, chokes, valves, or other control devices. These control devices may be located on the surface, under the surface (e.g., downhole in the wellbore), or any combination thereof. In some embodiments, the same control devices may be used to control fluid flow into and out of the wellbore, but different control devices may even be used. In some embodiments, the rate of flow of fluids through the wellbore may depend on the fluid handling capacities of the surface facility that is in fluidic communication with the wellbore. The control devices may also be utilized to control the pressure profile of the wellbore.

The equipment to be used in controlling fluid flow into and out of the wellbore may be dependent on the wellbore, the subsurface volume of interest, the surface facility, etc. However, for simplicity, the term "control apparatus" is meant to represent any wellhead(s), BOP(s), choke(s), valve(s), fluid(s), and other equipment and non-equipment items related to controlling fluid flow into and out of the wellbore.

The wellbore may be drilled into the subsurface volume of interest using practically any drilling technique and equipment known in the art, such as geosteering, directional drilling, etc. For example, drilling the wellbore may include using a tool such as a drilling tool. The drilling tool may include a drill bit and a drill string. Drilling fluid, such as drilling mud, may be used while drilling in order to cool the drill tool and remove cuttings. Other tools may also be used while drilling or after drilling, such as measurement-while-drilling (MWD) tools, seismic-while-drilling (SWD) tools, wireline tools, logging-while-drilling (LWD) tools, other downhole tools, etc. After drilling to a predetermined depth, the drill string and the drill bit are removed, and then the casing, the tubing, etc. may be installed according to the design of the wellbore.

The equipment to be used in drilling the wellbore may be dependent on the design of the wellbore, the subsurface volume of interest, the hydrocarbons, etc. However, for simplicity, the term "drilling apparatus" is meant to represent any drill bit(s), drill string(s), drilling fluid(s), and other equipment and non-equipment items related to drilling the wellbore.

The term "wellbore" may be used synonymously with the terms "borehole," "well," or "well bore." The term "wellbore" is not limited to any description or configuration described herein.

The term "proximate" is defined as "near". If item A is proximate to item B, then item A is near item B. For example, in some embodiments, item A may be in contact with item B. For example, in some embodiments, there may be at least one barrier between item A and item B such that item A and item B are near each other, but not in contact with each other. The barrier may be a fluid barrier, a non-fluid barrier (e.g., a structural barrier), or any combination thereof. Both scenarios are contemplated within the meaning of the term "proximate."

The terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%. Furthermore, a range may be construed to include the start and the end of the range. For example, a range of 10% to 20% (i.e., range of 10%-20%) includes 10% and also includes 20%, and includes percentages in between 10% and 20%, unless explicitly stated otherwise herein.

The term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein. By way of example, if an item is described herein as including a component of type A, a component of type B, a component of type C, or any combination thereof, it is understood that this phrase describes all of the various individual and collective combinations and permutations of these components. For example, in some embodiments, the item described by this phrase could include only a component of type A. In some embodiments, the item described by this phrase could include only a component of type B. In some embodiments, the item described by this phrase could include only a component of type C. In some embodiments, the item described by this phrase could include a component of type A and a component of type B. In some embodiments, the item described by this phrase could include a component of type A and a component of type C. In some embodiments, the item described by this phrase could include a component of type B and a component of type C. In some embodiments, the item described by this phrase could include a component of type A, a component of type B, and a component of type C. In some embodiments, the item described by this phrase could include two or more components of type A (e.g., A1 and A2). In some embodiments, the item described by this phrase could include two or more components of type B (e.g., B1 and B2). In some embodiments, the item described by this phrase could include two or more components of type C (e.g., C1 and C2). In some embodiments, the item described by this phrase could include two or more of a first component (e.g., two or more components of type A (A1 and A2)), optionally one or more of a second component (e.g., optionally one or more components of type B), and optionally one or more of a third component (e.g., optionally one or more components of type C). In some embodiments, the item described by this phrase could include two or more of a first component (e.g., two or more components of type B (B1 and B2)), optionally one or more of a second component (e.g., optionally one or more components of type A), and optionally one or more of a third component (e.g., optionally one or more components of type C). In some embodiments, the item described by this phrase could include two or more of a first component (e.g., two or more components of type C (C1 and C2)), optionally one or more of a second component (e.g., optionally one or more components of type A), and optionally one or more of a third component (e.g., optionally one or more components of type B).

The terms "length", "width", and "thickness" are illustrated in some of the figures to avoid confusion, such as FIG.

2H illustrated an embodiment of the test analysis system in cross section. Length refers from left to right. Thickness refers to top to bottom. Width refers to coming into or out of (e.g., the figure). Of course, those of ordinary skill in the art may also look at the context of a measurement if there is any confusion.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software, or any combination thereof.

Unless defined otherwise, all technical and scientific terms used herein have the same meanings as commonly understood by one of skill in the art to which the disclosed invention belongs. All citations referred herein are expressly incorporated by reference.

OVERVIEW: Proppant embedment at the fracture face may result in reduced hydrocarbon flow from the matrix into the fracture due to reduced pore throat size, crushing of rock, fines generation, pore plugging within the embedment zone (i.e., at the fracture face), or any combination thereof. The current API proppant conductivity test typically only measures conductivity losses that occur within the high permeability proppant pack due to fracture gel damage and reduction in fracture width due to stress. The damage at the fracture face cannot be measured by the API conductivity test. Of note, those of ordinary skill in the art will appreciate that the term "damage," as used herein, refers to reduced permeability (or zone of reduce permeability) due to multiple physical processes (e.g., crushing of rock, fines migration, geochemistry effects, etc.).

Embodiments consistent with the principles of the present invention may be used for determining formation damage at the fracture face due to proppant embedment and assess contribution of this damage to reduced production rates from a fracture. For example, the embodiments provided herein may be utilized for determining permeability reduction at the fracture face due to proppant embedment as a function depletion. The same test set-up can also be utilized for determining conductivity of the proppant pack. For example, the embodiments provided herein regarding this core test set-up represent: 1) the hydraulic fracture, 2) the proppant pack that lies within the fracture, 3) fluid flow from the matrix into the fracture, 4) measurement of permeability decline within the matrix at the frac face, and/or 5) conductivity decline in the proppant pack as a function of stress acting on the reservoir.

Embodiments provided herein may be utilized in determining a fluid characteristic, a test sample characteristic, or any combination thereof. At least one determined characteristic may be utilized for determining fracture face formation permeability (FFFP), conductivity (e.g., that accounts for proppant embedment), or any combination thereof. For example, the fluid characteristic, the test sample characteristic, or any combination thereof may be determined by embodiments of the test sample analysis system, and at least one determined characteristic may be utilized by a computing system, such as computer, for determining the FFFP, the conductivity, or any combination thereof. As another example, the fluid characteristic, the test sample characteristic, or any combination thereof may be determined by embodiments of the test sample analysis system, and at least one determined characteristic may be utilized by a user for determining the FFFP, the conductivity, or any combination thereof. As another example, the fluid characteristic, the test sample characteristic, or any combination thereof may be determined by embodiments of the test sample analysis system, and at least one determined characteristic may be utilized by a user and a computing system for determining the FFFP, the conductivity, or any combination thereof.

Provided herein include systems and methods that can measure formation damage at the fracture face as a function of different parameters and assess the impact on fluid production from a fracture. For example, provided herein are embodiments of systems and methods that may be used to determine fracture face formation permeability. Some embodiments may also be utilized to determine conductivity that accounts for proppant embedment.

In some embodiments, a system comprises a housing having a cavity defined therein for holding a test sample; a first inlet in fluid communication with the cavity to deliver fluid to the test sample; a second inlet in fluid communication with the cavity to deliver fluid to the test sample, the first inlet configured to deliver fluid to the test sample in a direction substantially perpendicular to a direction that the second inlet is configured to deliver fluid to the test sample; an outlet in fluid communication with the cavity to receive fluid from the test sample; and a force applicator configured to apply compressive force to the test sample within the cavity. The force applicator forms a seal with the housing while applying compressive force to the test sample. The system further comprises at least one sensor configured to, while fluid flows from at least one of the inlets through the test sample to the outlet, determine a fluid characteristic, a test sample characteristic, or any combination thereof.

In some embodiments, a system comprises a housing having a cavity defined therein for holding a test sample; a first inlet in fluid communication with the cavity to deliver fluid to the test sample; a second inlet in fluid communication with the cavity to deliver fluid to the test sample; a first shim in fluid communication with the second inlet, the first shim configured to distribute fluid that is delivered from the second inlet across a surface of the test sample such that fluid being distributed across the surface of the test sample is distributed in a direction substantially perpendicular to a direction that the first inlet is configured to distribute fluid to the test sample; an outlet in fluid communication with the cavity to receive fluid from the test sample; and a force applicator configured to apply compressive force to the test sample within the cavity. The force applicator forms a seal with the housing while applying compressive force to the test sample. The system further comprises at least one sensor configured to, while fluid flows from at least one of the inlets through the test sample to the outlet, determine a fluid characteristic, a test sample characteristic, or any combination thereof.

In some embodiments, a method comprises flowing fluid through a test sample using a first fluid inlet and a fluid outlet; flowing fluid through the test sample using another fluid inlet and the fluid outlet, wherein the first inlet is configured to deliver fluid to the test sample in a direction perpendicular to a direction that the other fluid inlet is configured to deliver fluid to the test sample; applying a compressive force to the test sample while fluid flows through the test sample; and while fluid flows from at least one of the inlets through the test sample to the fluid outlet, determining a fluid characteristic, a test sample characteristic, or any combination thereof.

Advantageously, those of ordinary skill in the art will appreciate, for example, that the systems and methods discussed herein may be utilized to improve a fracturing operation. For example, the embodiments provided herein may be utilized to select proppant, select fluid (e.g., select a fracturing fluid), etc. Additionally, the embodiments provided herein may lead to a more accurate assessment of proppant, such as indicating a lower conductivity for a particular type of proppant than expected for that type of proppant due to embedment and/or crushed core fines from the fracture face.

Advantageously, those of ordinary skill in the art will appreciate, for example, that the systems and methods discussed herein may lead to more reliable production forecasts, improvements in well performance assessment, reduction in uncertainty in production forecasting, improvements in well completion design (and optimization), higher quality intervention decisions, etc. Those of ordinary skill in the art will appreciate, for example, the embodiments may be utilized in hydrocarbon exploration and hydrocarbon production for decision making, improvements, optimization, etc. Those of ordinary skill in the art will appreciate, for example, that the embodiments may be utilized in hydrocarbon exploration and hydrocarbon production for control. As an example, the embodiments may be utilized for controlling flow of fluid injected into or received from the subsurface, the wellbore, or any combination thereof. Chokes or well control devices, positioned on the surface or downhole, may be used to control the flow of fluid into and out. For example, the embodiments may lead to activation, deactivation, modification, or any combination thereof of the chokes or well control devices so as control the flow of fluid. Thus, the embodiments to control injection rates, production rates, or any combination thereof. Those of ordinary skill in the art will appreciate, for example, that the embodiments may be utilized to select completions, components, fluid, proppants, etc. In short, those of ordinary skill in the art will appreciate that there are many decisions to make in the hydrocarbon industry and making proper decisions should improve the likelihood of safe and reliable operations.

FRACTURE FACE FORMATION PERMEABILITY (FFFP) SYSTEM OVERVIEW: Embodiments provided herein may be utilized in determining a fluid characteristic, a test sample characteristic, or any combination thereof. At least one determined characteristic may be utilized for determining fracture face formation permeability (FFFP), conductivity (e.g., that accounts for proppant embedment), or any combination thereof. For example, the fluid characteristic, the test sample characteristic, or any combination thereof may be determined by embodiments of the test sample analysis system, and at least one determined characteristic may be utilized by a computing system, such as computer, for determining the FFFP, the conductivity, or any combination thereof. As another example, the fluid characteristic, the test sample characteristic, or any combination thereof may be determined by embodiments of the test sample analysis system, and at least one determined characteristic may be utilized by a user for determining the FFFP, the conductivity, or any combination thereof. As another example, the fluid characteristic, the test sample characteristic, or any combination thereof may be determined by embodiments of the test sample analysis system, and at least one determined characteristic may be utilized by a user and a computing system for determining the FFFP, the conductivity, or any combination thereof. A portion or all of the test sample analysis system may be made of stainless steel.

Sensor—Fluid Characteristic—Test Sample Characteristic: In some embodiments, the test sample analysis system comprises at least one sensor configured to, while fluid flows from at least one of the inlets through the test sample to the outlet, determine (e.g., measure) a fluid characteristic, determine (e.g., measure) a test sample characteristic, or any combination thereof. In some embodiments, while fluid flows from at least one of the inlets through the test sample to the fluid outlet, the embodiments include determining a fluid characteristic, a test sample characteristic, or any combination thereof. For example, the test sample analysis system may be utilized to directly measure the fluid characteristic, to directly measure the test sample characteristic, or any combination thereof. Examples of the fluid characteristic include, but are not limited to, pressure of the fluid (e.g., linked to an inlet, linked to an outlet, etc.), temperature of the fluid, flow rate of the fluid, etc. In some embodiments, the computing system may utilize the pressure of the fluid and the temperature of the fluid to determine the viscosity of the fluid. The viscosity of the fluid may be utilized by the computing system to then determine FFFP, conductivity, or any combination thereof. Examples of the test sample characteristic include, but are not limited to, temperature of the test sample, temperature of a layer of porous media (e.g., layer of rock), thickness of the test sample (e.g., thickness of the rock and proppants), etc. The thickness of a particular layer of the test sample may be based on assumptions in deformation of the proppant and porous media. A user may make the assumptions and input the assumptions into the computing system, and then the computing system may determine FFFP.

The at least one sensor may be practically any sensor known in the art to determine the target characteristic. For example, a temperature related characteristic may be determined using a thermocouple, etc. The at least one sensor may be placed in various locations within the system, external to the system, etc. For example, a pressure sensor may be utilized to measure pressure and a separate sensor may be utilized to measure temperature.

In some embodiments, the first inlet may be coupled to at least one sensor to measure pressure, temperature, and flow rate. In some embodiments, the second inlet may be coupled to at least one sensor to measure pressure, temperature, and flow rate. In some embodiments, the third inlet may be coupled to at least one sensor to measure pressure, temperature, and flow rate. In some embodiments, the outlet may be coupled to at least one sensor to measure pressure and temperature. In some embodiments, the housing may be coupled to at least one sensor to measure the temperature of the housing. In some embodiments, at least one sensor may be coupled to the test sample analysis system to measure thickness (e.g., thickness of the entire test sample, thickness of a layer of the test sample using assumptions, or any combination thereof) and tilt to increase the likelihood that the fluid is injected vertically (e.g., without any inclines and without any declines). For example, a plurality of sensors, such as two sensors (e.g., two lasers), may be utilized and the tilt may be determined by comparing the relative values measured from the two sensors. The two lasers may be aimed over the force applicator (e.g., a piston).

Fracture Face Formation Permeability (FFFP): Turning to fracture face formation permeability (FFFP), as discussed herein, the fluid characteristic, the test sample characteristic, or any combination thereof may be determined by embodiments of the test sample analysis system, and at least one determined characteristic may be utilized by a computing system (e.g., a computer) for determining (e.g., calculating) the FFFP, the conductivity, or any combination thereof. As another example, the fluid characteristic, the test sample characteristic, or any combination thereof may be determined by embodiments of the test sample analysis system, and at least one determined characteristic may be utilized by a user for determining the FFFP, the conductivity, or any combination thereof. As another example, the fluid characteristic, the test sample characteristic, or any combination thereof may be determined by embodiments of the test sample analysis system, and at least one determined characteristic may be utilized by a user and a computing system for determining the FFFP, the conductivity, or any combination thereof.

Some embodiments include determining FFFP by flowing fluid through the test sample via the other fluid inlet and the fluid outlet. For example, the FFFP may be determined by a computing system, a user, or both using a determined characteristic using at least one determined characteristic (e.g., pressure of the fluid, temperature of the fluid, and the flow rate of the fluid, as well as the thickness of the layer of porous media proximate to the inlet that fluid is flowing through and the temperature of that same layer of porous media). The other fluid inlet is a second fluid inlet only or a third fluid inlet only. Alternatively, the other fluid inlet comprises a second fluid inlet and a third fluid inlet.

The API conductivity test may be utilized in these embodiments as long as it accounts for the differences discussed herein, such as API RP19C Measurement of Properties of Proppants Used in Hydraulic Fracturing and Gravel-packing Operations, API RP 19D Measuring the Long-term Conductivity of Proppants, or any combination thereof. For example, Darcy's Law may be utilized in some embodiments. Darcy's Law may be utilized by the computing system, the user, or any combination thereof to determine FFFP, including the using the following equation:

$$k = \frac{\mu Q t}{\Delta P A}$$

Q refers to (volumetric) flow rate, k refers to permeability, t refers to thickness of the test sample (such as vertical platen thickness), $\mu$ (mu) refers to viscosity of the fluid, A refers to length times width, and P refers to pressure. $\Delta P$ (delta P) refers to a difference in pressure. For example, $\mu$ (mu) may be calculated (e.g., by a computing system) based on pressure and temperature measured from the second inlet (e.g., inlet2) to the outlet by the test sample analysis system. Q is measured from the second inlet (e.g., inlet2) to the outlet by the test sample analysis system. Delta P is measured from the second inlet (e.g., inlet2) to the outlet by the test sample analysis system. A is considered constant at the beginning of the test and it is the surface area of the test sample (i.e., length times width of the platen). t is measured via one or more sensors (e.g., one or more lasers) by the test sample analysis system with assumptions on how to attribute the deformation). Darcy's law is discussed further in Additional embodiments of a test sample, a shim, and others are available in Karazincir et al., "Measurement of Reduced Permeability at Fracture Face Due to Proppant Embedment and Depletion," SPE 191653, 2018 SPE Annual Technical Conference and Exhibition in Dallas, Tex., Sep. 24-26, 2018, which is incorporated by reference.

In some embodiments, in order to calculate the permeability of the test sample, the following parameters are measured: (1) the flow rate across the system from both the first inlet to the outlet and from the second inlet to the outlet; (2) the temperature of the fluid and the temperature of the housing with all the components incapsulated within it; (3) the pressure drop across the first inlet to the outlet and from the second inlet to the outlet; (4) the width of the test sample throughout the test. The two measured temperatures are combined to calculate the viscosity of the fluid as it passes through the test sample and proppant. The resulting viscosity is then combined with the pressure drop, flow rate, and width to calculate the permeability of the test sample.

Fracture face formation permeability is the permeability associated with the reservoir rock in the region close to a hydraulic fracture or FracPack placed as part of the well completion. This encompasses the region where (1) the rock has intermingled with the proppant (Embedment Zone), (2) the crushed zone where the loading from proppant has caused damage to the rock matrix, and (3) the region where the loading from the flow pattern associated with the geometry of the fracture is represented. The reservoir rock in this region either experiences a change in properties or a significantly different loading path in comparison to rock that exists in the far field that can be represented by an uniaxial compaction loading condition.

In some embodiments, deriving the fracture face formation permeability is based on the utilization of Darcy's law assuming a linear flow pattern through three distinct zones across the core platen in series. 1. As the flow enters the core platen from the direction of the second inlet or the third inlet, there is an initial embedment/crushed zone where the core platen comes in contact with the proppant. 2. Beyond the initial embedment/crushed zone, the platen has a non-damaged permeability that is based on the amount of compaction under the selected load path. 3. As the flow exits the platen to the central proppant pack, then a second embedment zone is encountered with similar thickness and properties as the first. 4. In the field application, the first embedment zone would not exist. However, the top layer of proppant is utilized to distribute the flow over the large area core platen, and the mathematical treatment of the results can eliminate the impact of this initial area while retaining the impact of the other two.

Conductivity: Turning to conductivity, as discussed herein, the fluid characteristic, the test sample characteristic, or any combination thereof may be determined by embodiments of the test sample analysis system, and at least one determined characteristic may be utilized by a computing system (e.g., a computer) for determining (e.g., calculating) the FFFP, the conductivity, or any combination thereof. As another example, the fluid characteristic, the test sample characteristic, or any combination thereof may be determined by embodiments of the test sample analysis system, and at least one determined characteristic may be utilized by a user for determining the FFFP, the conductivity, or any combination thereof. As another example, the fluid characteristic, the test sample characteristic, or any combination thereof may be determined by embodiments of the test sample analysis system, and at least one determined characteristic may be utilized by a user and a computing system for determining the FFFP, the conductivity, or any combination thereof.

Some embodiments include running at least two conductivity tests such that the method comprises (1) flowing fluid through a test sample using a first fluid inlet and a fluid outlet; (2) subsequently, flowing fluid through the test sample using another fluid inlet and the fluid outlet, wherein the first inlet is configured to deliver fluid to the test sample in a direction perpendicular to a direction that the other fluid inlet is configured to deliver fluid to the test sample; (3) subsequently, flowing fluid through the test sample using the first fluid inlet and the fluid outlet (and applying a compressive force to the test sample while fluid flows through the test sample; and while fluid flows from at least one of the inlets through the test sample to the fluid outlet, determining a fluid characteristic, a test sample characteristic, or any combination thereof); and (4) using at least one determined characteristic (e.g., using at least one determined characteristic from the second flow of fluid through the first fluid inlet and the fluid outlet in (3)) to determine conductivity. In some embodiments, FFFP and conductivity do not need to be determined for (1) and (2), instead, the conductivity is determined for (3). The other fluid inlet is a second fluid inlet only or a third fluid inlet only. Alternatively, the other fluid inlet comprises a second fluid inlet and a third fluid inlet. By doing so, (4) or the second conductivity of the test sample accounts for proppant embedment within the porous media.

Alternatively, some embodiments include determining a conductivity of the test sample based on flowing fluid through the test sample via the first fluid inlet and the fluid outlet. For example, the conductivity may be determined by a computing system, a user, or both using a determined characteristic (e.g., pressure of the fluid, temperature of the fluid, and the flow rate of the fluid, as well as the thickness and length of the second layer of proppant in the center of the test sample).

The API conductivity test may be utilized in these embodiments as long as it accounts for the differences discussed herein, such as API RP19C Measurement of Properties of Proppants Used in Hydraulic Fracturing and Gravel-packing Operations, API RP 19D Measuring the Long-term Conductivity of Proppants, or any combination thereof. Darcy's law may be used for conductivity. For example, Darcy's Law may be utilized by the computing system, the user, or any combination thereof to determine conductivity, including the using the following equation:

$$k_p t_p = \frac{\mu Q_p L}{\Delta P_p w}$$

Q refers to (volumetric) flow rate through the proppant pack (e.g., the second layer of proppant in the center of the test sample/platen) and the subscript p stands for proppant pack, $k_p$ refers to permeability of the proppant pack, $t_p$ refers to thickness of the proppant pack, $\mu$ (mu) refers to viscosity of the fluid, and $P_p$ refers to pressure of the proppant pack. $\Delta P_p$ (delta $P_p$) refers to a difference in pressure in the proppant pack. For example, $\mu$ (mu) may be calculated (e.g., by a computing system) based on pressure and temperature measured from the first inlet (e.g., inlet1) to the outlet by the test sample analysis system. w is the width of the proppant pack. Q is measured from the first inlet (e.g., inlet1) to the outlet by the test sample analysis system. Delta $P_p$ is measured from the first inlet (e.g., inlet1) to the outlet by the test sample analysis system. $t_p$ is measured via one or more sensors (e.g., one or more lasers) by the test sample analysis system with assumptions on how to attribute the deformation. L is the length of the proppant pack from the first inlet (e.g., inlet1) to the outlet. Darcy's law is discussed further in Additional embodiments of a test sample, a shim, and others are available in Karazincir et al., "Measurement of Reduced Permeability at Fracture Face Due to Proppant Embedment and Depletion," SPE 191653, 2018 SPE Annual Technical Conference and Exhibition in Dallas, Tex., Sep. 24-26, 2018, which is incorporated by reference.

Inlet—Outlet: In some embodiments, the system comprises a first inlet and a second inlet. In some embodiments, the system comprises a first inlet and a third inlet. In some embodiments, the system comprises a first inlet, a second inlet, and a third inlet.

The first inlet is in fluid communication with the cavity to deliver fluid to the test sample. In some embodiments, the first inlet is configured to deliver fluid to the test sample in a direction substantially perpendicular to a direction that the other fluid inlet is configured to deliver fluid to the test sample. The other fluid inlet is a second fluid inlet only or a third fluid inlet only. The other fluid inlet comprises a second fluid inlet and a third fluid inlet. The second inlet is in fluid communication with the cavity to deliver fluid to the test sample. In some embodiments, the first inlet is configured to deliver fluid to the test sample in a direction substantially perpendicular to a direction that the second inlet is configured to deliver fluid to the test sample. The third inlet is in fluid communication with the cavity to deliver fluid to the test sample. In some embodiments, the third inlet is configured to deliver fluid to the test sample in a direction substantially opposite of the direction that the second inlet is configured to deliver fluid to the test sample. In some embodiments, the first inlet delivers fluid to a first side of the test sample, the second inlet delivers fluid to a top of the test sample, and the third inlet delivers fluid to a bottom of the test sample. In some embodiments, an outlet is in fluid communication with the cavity to receive fluid from the test sample.

In some embodiments, the first inlet comprises a plurality of inlets. In some embodiments, the second inlet comprises a plurality of inlets. In some embodiments, the third inlet comprises a plurality of inlets. In some embodiments, the outlet comprises a plurality of outlets. In some embodiments, the first inlet is a single inlet. In some embodiments, the outlet is a single outlet. In some embodiments, one or more of the inlets may include an injection port. The radius of the injection port may be 0.05 inches-0.4 inches in one embodiment, or about 0.2 inches in on embodiment. The outlet radius is about the same as the radius of the injection port.

The terms first inlet and first fluid inlet may be used interchangeably herein. The terms "outlet" and "fluid outlet" may be used interchangeably herein. The term "another inlet," "other inlet," "another fluid inlet," and "other fluid inlet" may be used interchangeably, and refer to the second inlet only in some embodiments, the third inlet only in some embodiments, or both the second inlet and the third inlet in some embodiments. For example, the other fluid inlet is a second fluid inlet or a third fluid inlet in some embodiments, but the other fluid inlet comprises a second fluid inlet and a third fluid inlet in some other embodiments. However, those of ordinary skill in the art will appreciate that this disclosure is not limited to the two inlet and three inlet embodiments discussed herein.

Shim: In some embodiments, the system comprises at least one shim configured to distribute fluid delivered from one of the inlets across a surface of the test sample. For example, some embodiments may include two shims. In a particular embodiment, the plurality of shims may be the same. In a particular embodiment, the plurality of shims may be different, for example, there may be at least one difference between two shims.

In some embodiments, the shim is made of stainless steel, such as corrosion resistant steel, acid resistant steel, and the like. In some embodiments, the shim has the following dimensions: a length of about 7 inches in one embodiment, a length of 6 inches-8 inches in one embodiment; a width of about 1.5 inches in one embodiment, a width of 1 inch-2 inches in one embodiment, a thickness of about 1 mm in one embodiment, a thickness of 0.5 mm-2 mm in one embodiment. Of note, the dimensions of the shim will depend on the dimensions of the housing to allow for fluid distribution across a surface of the test sample.

In some embodiments, the shim comprises grooves to distribute fluid across a surface of the test sample. For example, the grooves may be located on the outer surface of the shim closest to the test sample to connect flow from the three injection ports (e.g., from the inlet2 having three inlets). The grooves may keep open flow paths on the core face while under loading, such that the flow paths follow the grooves on the shim. Thus, the grooves may increase the likelihood of keeping at least one open flow path with loading. The dimensions and locations of the grooves may also depend on the desired fluid distributions. In some embodiments, the grooves may be .5 mm-1 mm depending on the thickness of the corresponding shim.

In some embodiments, the shim comprises an opening through the shim, and an outer surface of the shim comprises grooves proximate to the opening. In some embodiments, the grooves comprise a circular groove with the opening in a center of the circular groove, a letter x groove with the opening in a center of the letter x groove, a vertical line groove extending lengthwise from the opening on the outer surface of the shim, a first horizontal line groove at a first intersection of the circular groove and the vertical line groove that extends widthwise on the outer surface of the shim, a second horizontal line groove at a second intersection of the circular groove and the vertical line groove that extends widthwise on the outer surface of the shim, and a third horizontal line groove extending widthwise from the opening on the outer surface of the shim. In some embodiments, the shim comprises a plurality of openings through the shim, and an outer surface of the shim comprises grooves proximate to each opening. For example, each opening may have a corresponding circular groove, a corresponding letter x groove, a corresponding vertical line groove, etc. In some embodiments, the shim may have three openings, and each opening has a corresponding circular groove, a corresponding letter x groove, a corresponding vertical line groove, etc. However, those of ordinary skill in the art will appreciate that other grooves may be utilized in some embodiments.

In some embodiments, the system comprises a first shim configured to distribute fluid delivered from the second inlet across a surface of the test sample. In some embodiments, a first shim is in fluid communication with the second inlet, and the first shim is configured to distribute fluid that is delivered from the second inlet across a surface of the test sample such that the fluid being distributed across the surface of the test sample is distributed in a direction substantially perpendicular to a direction that the first inlet is configured to distribute fluid to the test sample.

In some embodiments, the system also comprises a second shim configured to distribute fluid delivered from the third inlet across a surface of the test sample. In some embodiments, a second shim is in fluid communication with the third inlet, the second shim is configured to distribute fluid that is delivered from the third inlet across a second surface of the test sample such that the fluid being distributed across the second surface of the test sample is distributed in a direction substantially opposite to a direction that the first shim is configured to distribute fluid to the test sample.

In some embodiments, the first shim in fluid communication with the second inlet distributes fluid across a top surface of the test sample, and the second shim in fluid communication with the third inlet distributes fluid across a bottom surface of the test sample.

Fluid: In some embodiments, the fluid comprises brine. In some embodiments, the fluid comprises hydrocarbons. In some embodiments, the fluid comprises brine and hydrocarbons (e.g., oil). In some embodiments, the fluid may comprise gas. In some embodiments, the fluid may comprise multiple phases, such as two phases. In some embodiments, the fluid may comprise one phase. In some embodiments, the fluid may comprise acid, such as HF acid. In some embodiments, the fluid may comprise an injection fluid, such as fracturing fluid (e.g., borate fracturing fluid). The fluid (e.g., brine) may be after acid.

Proppant: In some embodiments, the proppant are made by nature, such as sand. In some embodiments, the proppant are manufactured. In some embodiments, the proppant comprises naturally made proppant and manufactured proppant. In some embodiments, the proppant may comprise the HSP brand or the Kryptosphere brand of proppant by Carbo Ceramics Inc.

In some embodiments, the test sample includes at least one layer of proppant. For example, the test sample may include a first layer of proppant between the first shim and a first layer of porous media of the test sample to help the flow distribution and increase the inflow area. For example, the first layer of proppant between the first shim and the first layer of porous media may be at least 0.1 inch thick (e.g., 0.1 inch-0.2 inch thick) to distribute fluid flow at the core face. For example, the first layer of proppant between the first shim and the first layer of porous media may be 0.2 inch thick or less (e.g., 0.1 inch-0.2 inch thick) to distribute fluid flow at the core face. A third layer of proppant between the second shim and a second layer of porous media of the test sample may have similar characteristics.

In some embodiments, the test sample may include a second layer of proppant between two porous media layers. The second layer of proppant between the two porous media layers (e.g., the first layer of porous media and the second layer of porous media) may be thicker than the first layer of proppant proximate to the first shim in one embodiment. The second layer of proppant between the two porous media layers may be thicker than the third layer of proppant proximate to the second shim in one embodiment. The second layer of proppant between the two porous media layers may be thicker than the first layer of proppant proximate to the first shim and the third layer of proppant proximate to the second shim in one embodiment.

In some embodiments, the test sample may include a plurality of proppant layers, such as two proppant layers or three proppant layers.

Test Sample: The test sample may be referred to as a "core", a "core wafer", a "platen", a "core sample", or the like. In some embodiments, the test sample comprises at least one layer of porous media and at least one layer of proppant. In some embodiments, the test sample comprises at least one layer of porous media and at least one layer of proppant, and the at least one layer of proppant is positioned between a first layer of porous media and a second layer of porous media. In some embodiments, the test sample comprises layers of porous media and proppant, and the top and bottom surfaces of the test sample comprise layers of proppant. In some embodiments, the test sample comprises layers of porous media and proppant, and fluid is delivered first to a layer of proppant. In some embodiments, the test sample comprises: a first layer of proppant, a second layer of proppant, a first layer of porous media between the first and second layers of proppant, a third layer of proppant, and a second layer of porous media between the second and third layers of proppant. The layer(s) of proppant is discussed further herein.

In some embodiments, the system comprises a first shim configured to distribute fluid delivered from the second inlet across a surface of the test sample, and the test sample comprises at least one layer of porous media and at least one layer of proppant such that the at least one layer of proppant is positioned between the at least one layer of porous media and the first shim.

In some embodiments, the system comprises a second shim configured to distribute fluid delivered from the third inlet across a second surface of the test sample, and the test sample comprises at least one layer of porous media and at least one layer of proppant such that the at least one layer of proppant is positioned between the at least one layer of porous media and the second shim.

In some embodiments, the test sample may have a length of about 6.967 inches. In some embodiments, the test sample may have a length of at least five inches (e.g., 5 inches-8 inches). In some embodiments, the test sample may have length of 8 inches or less (e.g., 5 inches-8 inches). For example, the test sample may have a length of 5 inches to 7 inches in one embodiment, 5 inches-8 inches in a second embodiment, 5 inches-9 inches in a third embodiment, 6 inches-7 inches in a fourth embodiment, or 6 inches-8 inches in a fifth embodiment. In some embodiments, the test sample may be at least 1.5 inches thick (e.g., 1.5 inches-2 inches). In some embodiments, the test sample may be at least 2 inches thick (e.g., 2 inches-4 inches). In some embodiments, the test sample may be 4 inches or less thick (e.g., 1.5 inches-4 inches). The test sample may be 1.5 inches-2 inches think in one embodiment, 1.5 inches-4 inches thick in a second embodiment, 1.5 inches-3 inches thick in a third embodiment, or 2 inches-3 inches in a fourth embodiment. For example, a minimum thickness of 2 inches may increase the likelihood that the flow reaches linear flow regime inside the test sample.

In some embodiments, the porous media may be a piece of the formation or substantially similar to the formation. For example, the porous media may be a core sample extracted from the formation, a sand pack, etc. such that it is representative of a portion of the formation.

Housing—Cavity: In some embodiments, the system comprises a housing having a cavity defined therein for holding the test sample. In some embodiments, the housing is made of stainless steel, such as corrosion resistant steel, acid resistant steel, and the like. In some embodiments, the housing has the following dimensions: a length of about 10 inches in one embodiment, a length of 10 inches-14 inches in one embodiment, a thickness of 7 inches-10 inches in one embodiment, a width of 5 inches-7 inches in one embodiment. The dimensions of the housing may depend on the dimensions of the test sample.

Epoxy: In some embodiments, an epoxy is utilized for coating a surface. In some embodiments, at least a portion of an outer surface of the test sample is coated with epoxy such that the epoxy forms one or more seals between the outer surface of the test sample and the housing to prevent fluid flow therebetween. The epoxy between the test sample and the housing may also prevent rock failure under compressive force. For example, without epoxy support, the test sample may be in an unconfined deformation state, and therefore, the test sample may fail before the lateral deformation reaches the housing. The epoxy can fill a gap (e.g., a 0.01" gap) between the test sample and the housing, and this eliminates, or at a minimum, may reduce the proportion of the loading time under which the test sample is exposed to unconfined compression by ensuring contact from the onset of the test such that the test sample is under uniaxial compression for the whole test.

As described further herein, the test sample may vary. In some embodiments, the test sample comprises at least one layer of porous media and at least one layer of proppant. In some embodiments, at least a portion of an outer surface of at least one layer of porous media is coated with an epoxy. For example, assume that the test sample comprises 5 layers: a first layer of proppant; a second layer of proppant; a first layer of porous media between the first and second layers of proppant; a third layer of proppant; and a second layer of porous media between the second and third layers of proppant. The epoxy may be applied to an outer surface of each of the layers of porous media.

However, in some embodiments, at least a portion of an outer surface of at least one layer of proppant may be coated with an epoxy. In some embodiments, at least a portion of an outer surface of each layer of test sample may even be coated with an epoxy.

The epoxy may be applied to the test sample (or a layer thereof) before the test sample is inserted into the cavity of the housing. Alternatively, the epoxy may be applied to the test sample (or a layer thereof) after the test sample is inserted into the cavity, for example, by injection the epoxy into a gap between the test sample (or a layer thereof) and the housing. In some embodiments, a layer of epoxy is sufficient to fill in a gap between a layer of the test sample and the housing. In some embodiments, the layer of epoxy may be sufficient to fill a gap of about 0.01 inches.

In some embodiments, the epoxy is available from Henkel Corp., Loctite EA9490, underwater repair, Part No. 82093. However, those of ordinary skill in the art will appreciate that another epoxy may be utilized in some embodiments.

Force Applicator: In some embodiments, the system comprises a force applicator configured to apply compressive force to the test sample within the cavity such that the force applicator forms a seal with the housing while applying compressive force to the test sample. For example, the compressive force is applied to the test sample while fluid flows through the test sample. In some embodiments, the force applicator is a T-shaped piston. In some embodiments, the force applicator is made of stainless steel, such as corrosion resistant steel, acid resistant steel, or the like. In some embodiments, the force applicator has the following dimensions: a length of about 7 inches in one embodiment, a thickness of about 4 inches in one embodiment, a width of about 1.5 inches in one embodiment. In some embodiments, a ring or other mechanism (e.g., an O ring with a corresponding length and width of the force applicator) may be positioned around the force applicator (e.g., a piston) to create a seal with the housing. If the dimensions of the force applicator change, then the dimensions of the ring may change in a corresponding manner.

Heating Element: In some embodiments, the system comprises at least one heating element configured to heat the test sample while fluid flows through the test sample. The heating element may be practically any heater. The heating element may heat up the fluid and the test sample so as to mimic reservoir temperature. In some embodiments, the test sample may be heated to a sufficient number of degrees to mimic reservoir temperature, such as heating the fluid and the test sample to 150° F.-260° F. In some embodiments, the heating element may heat the fluid and the test sample to up to 300° F.

Embodiments: FIG. 1A illustrates an expanded view, in cross-section, of one embodiment of a hydrocarbon exploration and hydrocarbon recovery system 100 for which to determine fracture face formation permeability, conductivity, or any combination thereof. The wellbore 105 includes a horizontal section 115, and therefore, the wellbore 105 may be referred to as a horizontal wellbore. The wellbore 105 includes a vertical section 110, a build section 112, and the horizontal section 115. The area between the vertical section 110 and the horizontal section 115 is referred to as the heel and the area towards the end of the horizontal section 115 is referred to as the toe. For example, unconventional reservoirs may be produced using horizontal wellbores, such as the wellbore 105.

The wellbore 105 may be drilled with at least one drilling apparatus 113 through subsurface volume of interest (formation) 101. The drilling apparatus 113 may include a drill bit, a drill string, etc. The drilling apparatus 113 may be utilized to drill at least one other wellbore, drill at least one other track, or any combination thereof. The wellbore 105 may be cemented as illustrated by cement 106. The wellbore 105 may include a surface casing 120 along a portion of the wellbore 105, a production casing 125 along a portion of the wellbore 105, and a liner 130 (e.g., a slotted liner) attached by at least one liner hanger 132. At least one packer 170 may be located in an annulus 169 between the tubing 145 and the liner 130.

In operation, the wellbore 105 may be utilized for fracturing, including opening existing fractures and/or creating fractures, that lead to fractures 50 in the subsurface volume of interest 101. For example, a perforation apparatus may be deployed in a desired location in the wellbore 105 to generate perforations through one or more layers of the wellbore 105, and then fracturing apparatus 116 may be used to open and/or create the fractures 50. The fracturing fluid for the fractures 50 (e.g., with the proppant) may be injected using methodologies and equipment known in the art, and the flowback from the fractures 50 may be removed using methodologies and equipment known in the art. Fracturing may occur in stages with clusters in some embodiments.

After flowback, the hydrocarbons from the subsurface volume of interest 101 flow into the wellbore 105 through one or more of the fractures 50 and up a tubing 145 towards the surface 140 for refining, transporting, etc. For example, the wellbore 105 may also include a tubing 145 (e.g., production tubing for hydrocarbon production) within the surface casing 120, the production casing 125, and the liner 130. The tubing 145 may be of standard sizes known in the industry (e.g., outermost diameter of 2-⅜ inches to 4.5 inches) for standard and commonly known casing sizes (e.g., outermost diameter of 4-½ inches to 12 inches), each of which have lengths in the tens to hundreds of feet. The tubing 145 includes a plurality of tubulars tubing joints, pup joints, packers (e.g., may include centralizers), etc. The end of the tubing 145 (e.g., at the toe) may include a bull plug 150.

Figure 1B:
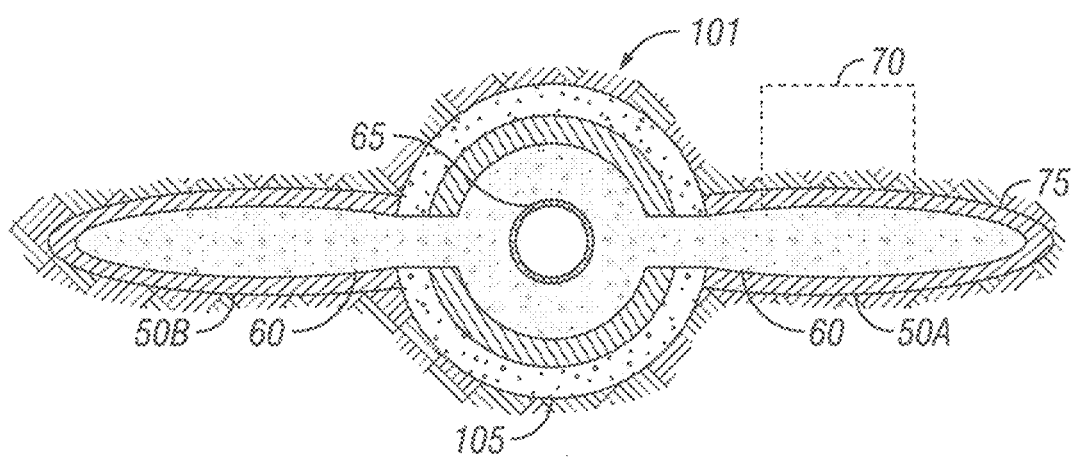
FIG. 1B illustrates a more detailed view of FGI. 1A.
Figure 21:
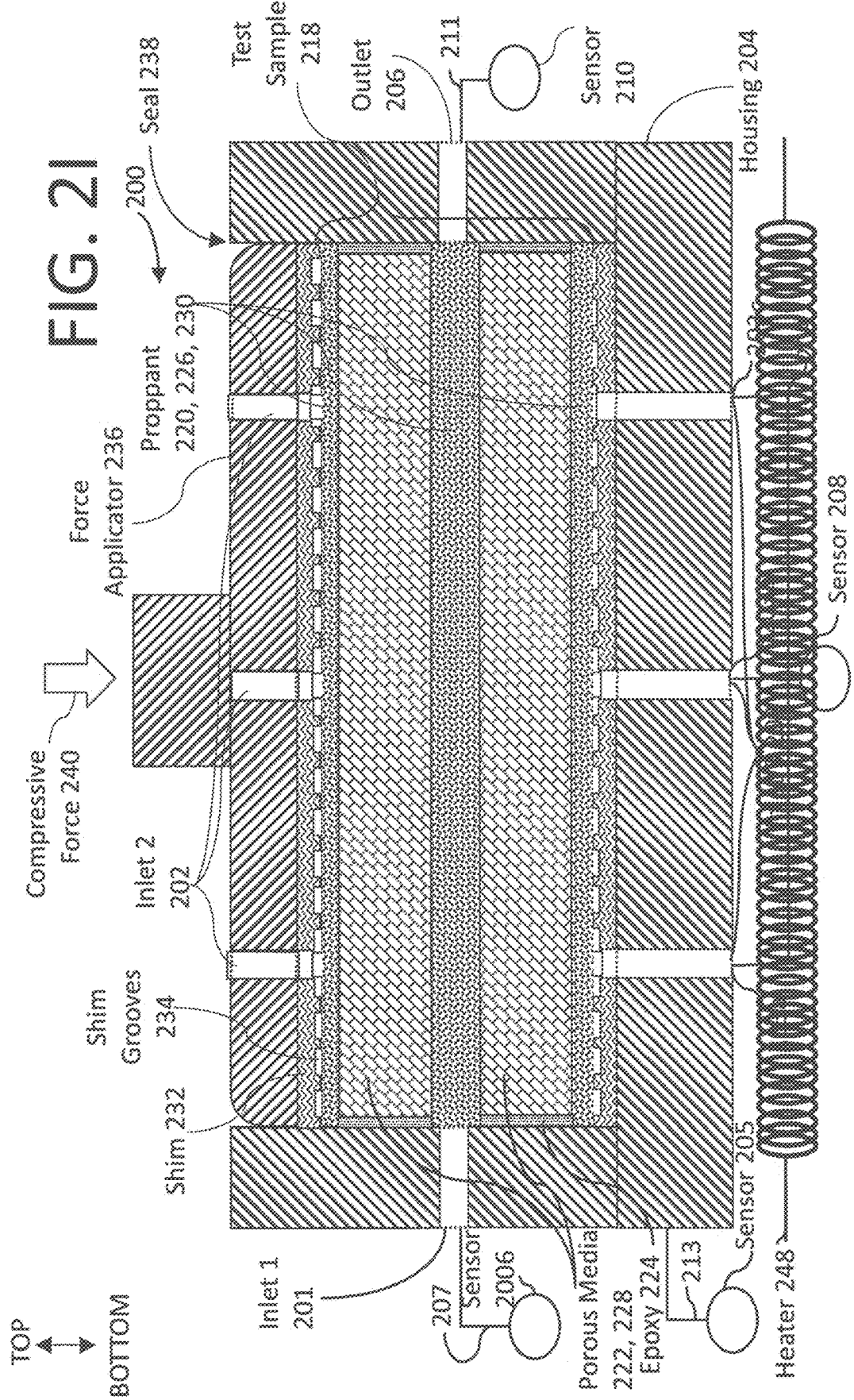

FIG. 1B illustrates an expanded view of a fracture 50a, a fracture 50b, and the wellbore 105. Proppant 60, such as a plurality of sand particles, flow from the wellbore 105 into each of the fracture 50a and the fracture 50b. Turning to the fracture 50a, the fracture 50a comprises a fracture face formation region 70 where at least a portion of the proppant 60 may be proximate to the region 70. At least a portion of the proppant 60 may also embed or get crushed in an embedment & crushed zone 75. The wellbore 105 may also include a screen 65. Embodiments of a test sample analysis system 200, such as illustrated in FIGS. 2A-2Q and 2R-B, may be utilized to determine fracture face formation permeability (FFFP), conductivity (e.g., that accounts for proppant embedment), or any combination thereof.

Turning to FIGS. 2A-2Q and 2R-B, these figures illustrate at least one embodiment of the test sample analysis system 200 that may be utilized in determining a fluid characteristic, a test sample characteristic, or any combination thereof. At least one determined characteristic may be utilized for determining fracture face formation permeability (FFFP), conductivity (e.g., that accounts for proppant embedment), or any combination thereof. FIGS. 2RA-2RB visually illustrates the difference between the typical API test and the instant embodiments. For example, in the typical API test, fluid only flows parallel to the fracture. However, the test sample analysis system 200 allows fluid to flow parallel and perpendicular to the fracture, which may improve accuracy and may lead to calculations that were not capable with the typical API test. As illustrated herein, fluid may flow through a first inlet such as an inlet1 referred to as 201 and a second inlet such as an inlet2 referred to as 202 of the test sample analysis system 200 in some embodiments (e.g., FIG. 2N). In the illustrated embodiments, the inlet2 202 comprises a plurality of inlets referred to as 202a, 202b, and 202c. Fluid may flow through the inlet1 201 and a third inlet such as an inlet3 referred to as 203 of the test sample analysis system 200 in some embodiments (e.g., FIG. 2O). In the illustrated embodiments, the inlet3 203 comprises a plurality of inlets referred to as 203a, 203b, and 203c. Fluid may flow through the inlet1 201, the inlet2 202, and the inlet3 203 in some embodiments (e.g., FIG. 2P).

Turning to FIGS. 2A-2Q and 2R-B, the test sample analysis system 200 includes a housing 204 that includes the inlet1 201, the inlet3 203 (including 203a, 203b, and 203c), and an outlet 206. At least one sensor 2006 is coupled to the inlet1 201 via a line 207. At least one sensor 208 is coupled to the inlet3 203 via a line 209. For example, a single temperature sensor 208 may be coupled to each of the inlet3 203a, 203b, and 203c via the line 209. For example, a single pressure sensor 208 may be coupled to each of the inlet3 203a, 203b, and 203c via the line 209. At least one sensor 210 is coupled to the outlet 210 via a line 211. At least one sensor 205 may also be coupled to the housing via a line 213.

The housing 204 includes a cavity 212. Various components may be positioned in the cavity 212, including a second shim 214 that comprises shim grooves 216. As illustrated, the second shim 214 includes three openings that correspond to the inlet3 203a, 203b, and 203c. A test sample 218 is proximate to the second shim 214. As illustrated, the test sample 218 includes five layers, and a third layer of proppant 220 of the test sample 218 is proximate to the second shim 214. A second layer of porous media 222 of the test sample 218 is proximate to the third layer of proppant 220. The outer surface of the second layer of porous media 222 is coated with an epoxy 224 to create one or more seals with the housing 204. A second layer of proppant 226 of the test sample 218 is proximate to the second layer of porous media 222. A first layer of porous media 228 of the test sample 218 is proximate to the second layer of proppant 226. The outer surface of the first layer of porous media 228 is coated with the epoxy 224 to create a seal with the housing 204. A first layer of proppant 230 of the test sample 218 is proximate to the first layer of porous media 228. As illustrated, the first layer of porous media 228 is located between the first layer of proppant 230 and the second layer of proppant 226, and the second layer of porous media 222 is located between the second layer of proppant 226 and the third layer of proppant 220.

A first shim 232 that comprises shim grooves 234 is proximate to the first layer of proppant 230 of the test sample 218. A force applicator 236 is proximate to the first shim 232 and forms one or more seals 238 with the housing 204. Compressive force 240 is applied to the force applicator 236. The force applicator 236 includes the inlet2 202, including the inlet2 202a, 202b, and 202c. At least one sensor 242 is coupled to the inlet2 202 via a line 243. For example, a single temperature sensor 242 may be coupled to each of the inlet2 202a, 202b, and 202c via the line 243. The first shim 232 also includes three openings that correspond to the inlet2 202a, 202b, and 202c. In some embodiments, a ring or other mechanism may be positioned around the force applicator 236 to form the seal 238. At least one sensor, such as lasers 244, 246, may also be positioned so as to aim at the force applicator 236 for determining thickness, tilt, or any combination thereof. In some embodiments, a heating element, such as a heater 248, may be positioned proximate to the housing 204 (e.g., opposite the force applicator 236) to heat the test sample 218.

Figure 2M:
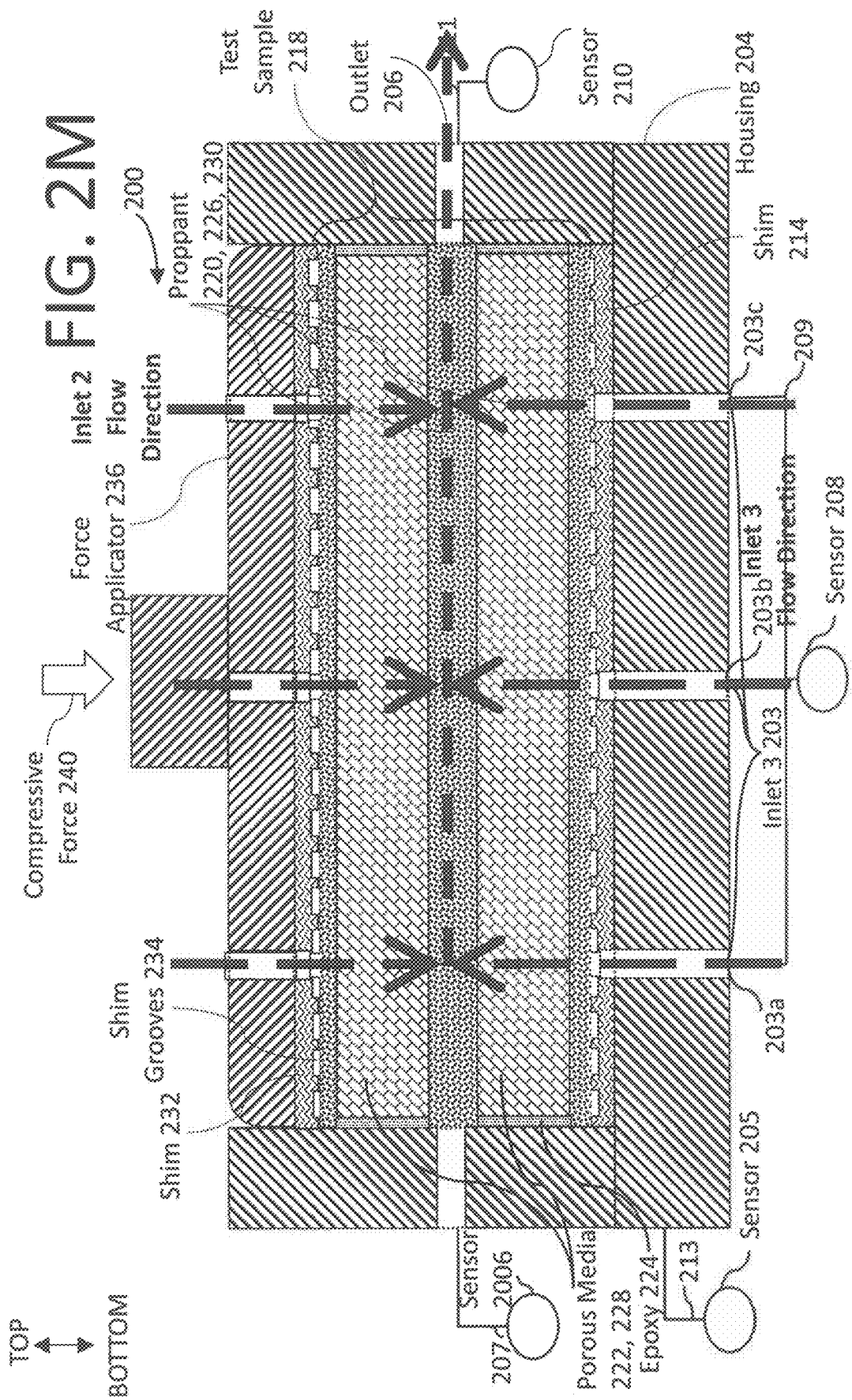
Figure 2Q:
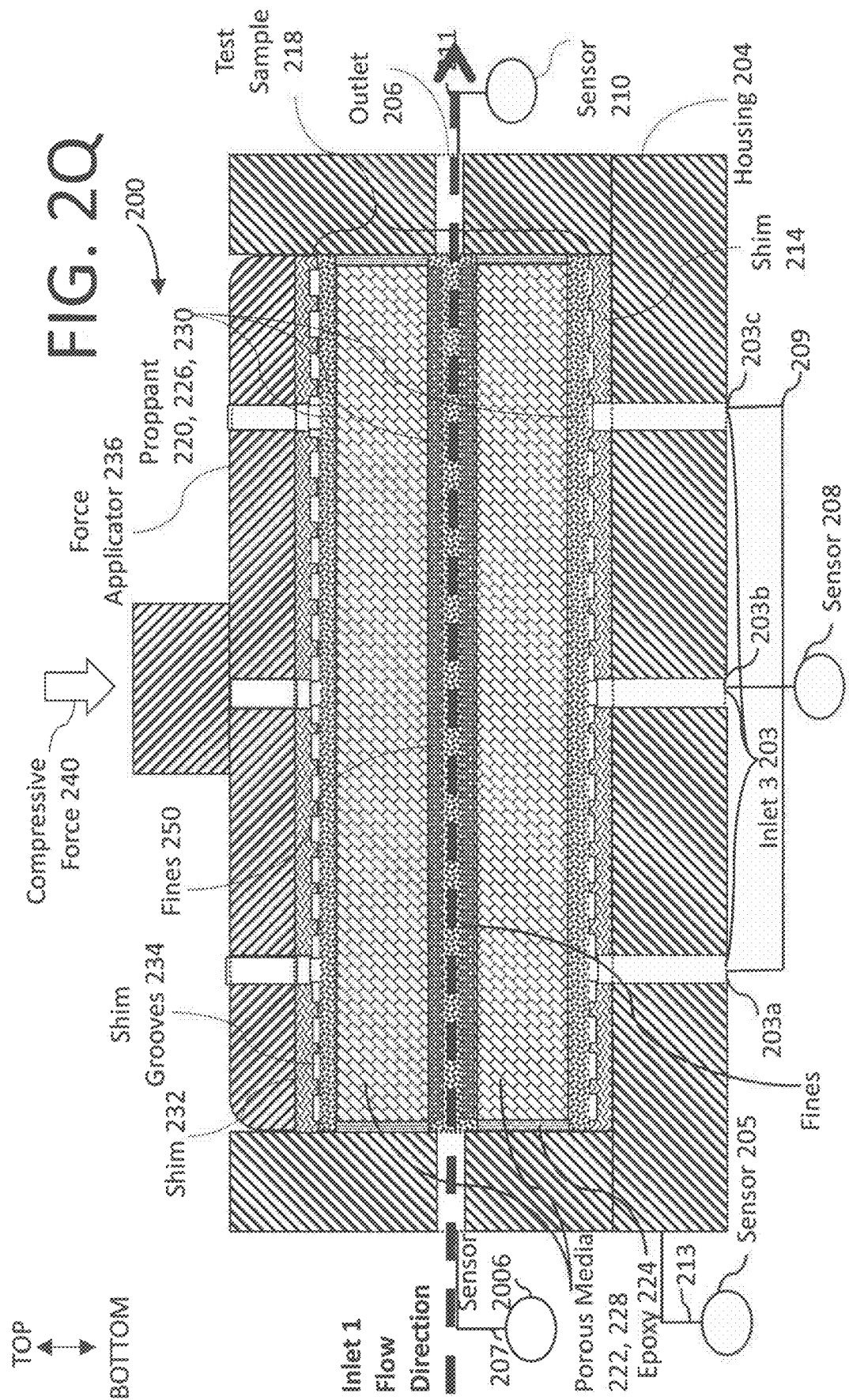

The inlet1 201 delivers fluid to a first side of the test sample 218, the inlet2 202 delivers fluid to a top of the test sample 218, and the inlet3 203 delivers fluid to a bottom of the test sample 218. FIG. 2J illustrates that the fluid may flow through the inlet1 201, the second layer of proppant 226, and the outlet 206. FIG. 2K illustrates that the fluid may flow through the inlet1 201, the inlet2 202, the second layer of proppant 226, and the outlet 206. FIG. 2K illustrates that the fluid may flow through the inlet2 202 (202a, 202b, 202c), the second layer of proppant 226, and the outlet 206. FIG. 2L illustrates that the fluid may flow through the inlet3 203 (203a, 203b, 203c), the second layer of proppant 226, and the outlet 206. FIG. 2M illustrates that the fluid may flow through the inlet2 202 (202a, 202b, 202c), the inlet3 203 (203a, 203b, 203c), the second layer of proppant 226, and the outlet 206. FIG. 2N illustrates that the fluid may flow through the inlet2 202 (202a, 202b, 202c), the inlet1 201 (201a, 201b, 201c), the second layer of proppant 226, and the outlet 206. FIG. 2O illustrates that the fluid may flow through the inlet3 203 (203a, 203b, 203c), the inlet1 201 (201a, 201b, 201c), the second layer of proppant 226, and the outlet 206. FIG. 2P illustrates that the fluid may flow through the inlet3 203 (203a, 203b, 203c), the inlet1 201 (201a, 201b, 201c), the inlet2 202 (202a, 202b, 202c), the second layer of proppant 226, and the outlet 206. FIG. 2Q illustrates that fines 250 may migrate into the second layer of proppant 226, which may reduce permeability. Of note, the order to flow the fluid may depend on the desired characteristics to be determined, on the desired test, etc. In some embodiments, the order that the fluid flows may not be important.

Figure 4A:
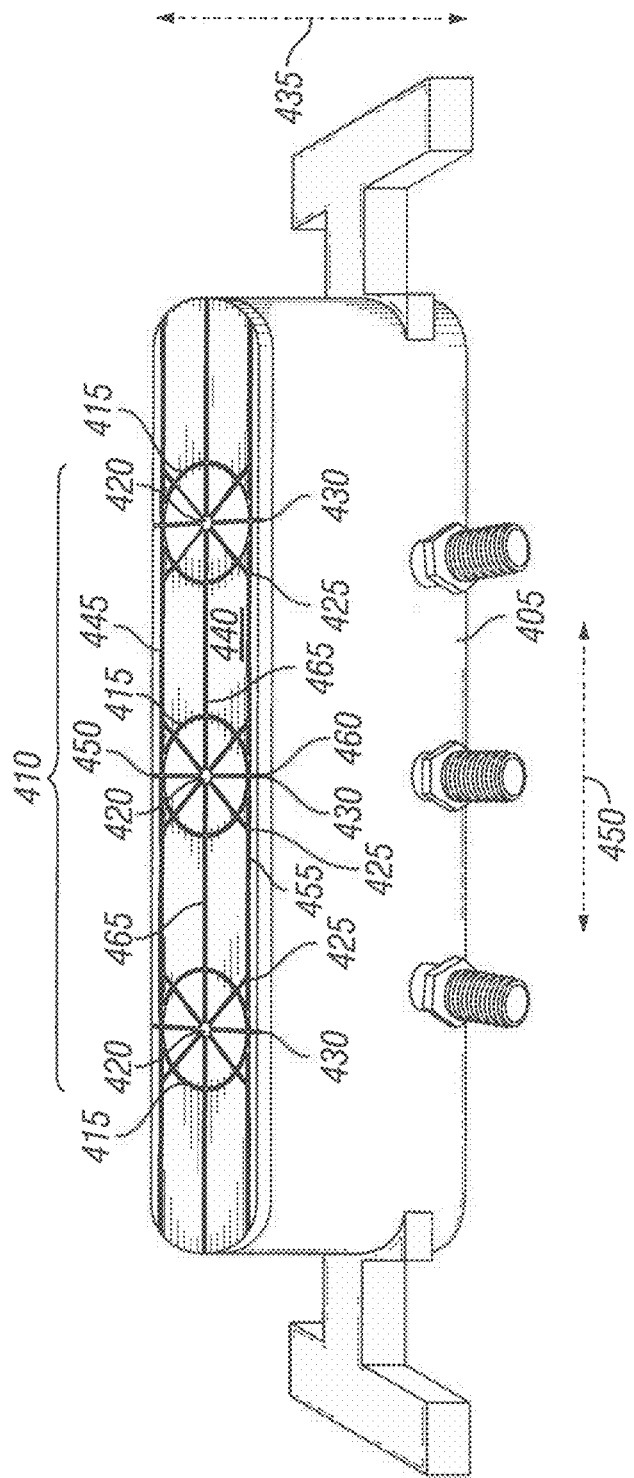
FIG. 4A illustrates one embodiment of a shim of the system.
Figure 4B:
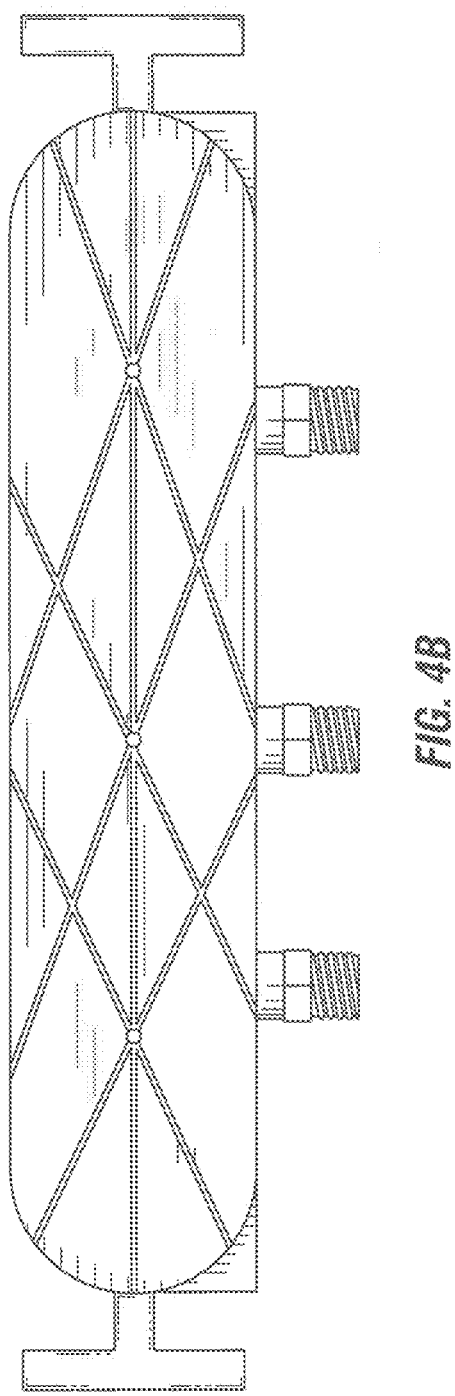
FIG. 4B illustrates another embodiment of a shim.

FIG. 4A illustrates one embodiment of a shim 405. As illustrated, grooves 410 comprise a circular groove 415 with the opening 420 in a center of the circular groove 415, a letter x groove 425 with the opening 420 in a center of the letter x groove 425, a vertical line groove 430 extending lengthwise 435 from the opening 420 on the outer surface 440 of the shim 405, a first horizontal line groove 445 at a first intersection 450 of the circular groove 415 and the vertical line groove 430 that extends widthwise 450 on the outer surface 440 of the shim 405, a second horizontal line groove 455 at a second intersection 460 of the circular groove 415 and the vertical line groove 430 that extends widthwise 450 on the outer surface 440 of the shim 405, and a third horizontal line groove 465 extending widthwise 450 from the opening 420 on the outer surface 440 of the shim 405. FIG. 4B illustrates another embodiment of a shim. One or both shims 214, 232 illustrated herein may be the shim 405 of FIG. 4A or the shim of FIG. 4B, but it is not necessary.

Additional embodiments of a test sample, a shim, and others are available in Karazincir et al., "Measurement of Reduced Permeability at Fracture Face Due to Proppant Embedment and Depletion," SPE 191653, 2018 SPE Annual Technical Conference and Exhibition in Dallas, Tex., Sep. 24-26, 2018, which is incorporated by reference. For example, additional embodiments are provided in FIG. 4, FIG. 11, and FIG. 18, as well as the text corresponding to each of these figures, of Karazincir et al. This paper also discuss some of the differences of the embodiments of the test analysis system compared to existing systems and methodologies.

Figure 3:
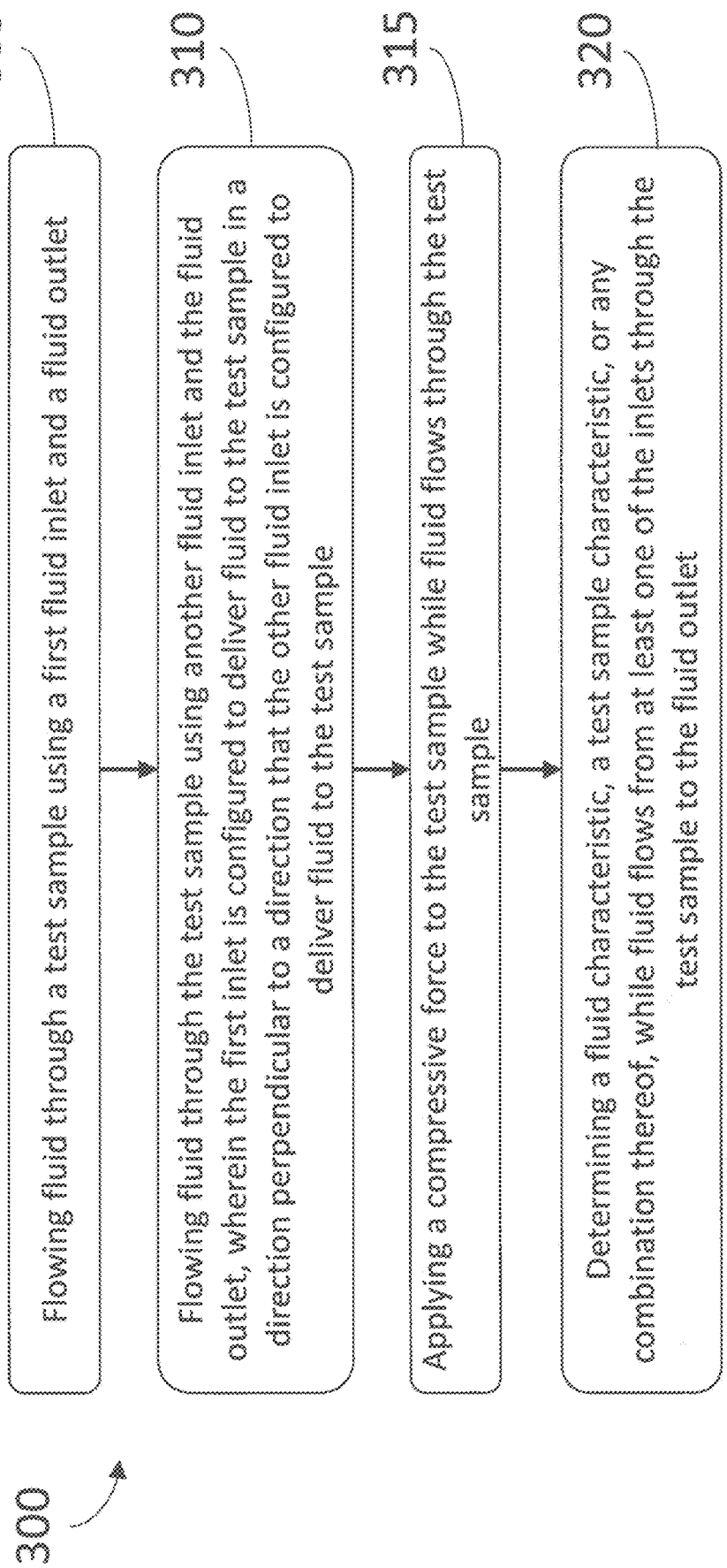

Turning to FIG. 3, this figure illustrates one embodiment of a method 300. At 305, the method comprises flowing fluid through a test sample using a first fluid inlet and a fluid outlet. At 310, the method comprises flowing fluid through the test sample using another fluid inlet and the fluid outlet, wherein the first inlet is configured to deliver fluid to the test sample in a direction perpendicular to a direction that the other fluid inlet is configured to deliver fluid to the test sample. In some embodiments, the other fluid inlet is a second fluid inlet only or a third fluid inlet only. In some embodiments, the other fluid inlet comprises a second fluid inlet and a third fluid inlet. At 315, the method comprises applying a compressive force to the test sample while fluid flows through the test sample. At 320, the method comprises, while fluid flows from at least one of the inlets through the test sample to the fluid outlet, determining a fluid characteristic, a test sample characteristic, or any combination thereof.

As discussed herein, the fluid characteristic, the test sample characteristic, or any combination thereof may be determined by embodiments of the test sample analysis system, and at least one determined characteristic may be utilized by a computing system (e.g., a computer) for determining (e.g., calculating) the FFFP, the conductivity, or any combination thereof. In some embodiments, the sensor data (e.g., pressure) from at least one sensor of the test sample analysis system 200 may get recorded and downloaded later. Alternatively, or additionally, in some embodiments, the sensor data from at least one sensor of the test sample analysis system 200 may be sent to a computing system 198, as illustrated in FIG. 1C. The computing system 198 may be coupled to the test sample analysis system 200 in a wireless manner, a wired manner, or any combination thereof as illustrated by a connection 181, and the computing system 198 determines the fracture face formation permeability, the conductivity or any combination thereof. In some embodiments, the calculation(s) may even be performed using a spreadsheet. Nonetheless, the sensor data may subsequently be used to determine the fracture face formation permeability, the conductivity, or any combination thereof.

The computing system 198 may be co-located with the test sample analysis system 200 or located remote from the system 198. One embodiment of the computing system 198 includes a processor 180 communicatively connected to a memory 182 via a data bus 184. The processor 180 may be any of a variety of types of programmable circuits capable of executing computer-readable instructions to perform various tasks, such as mathematical and communication tasks. The computing system 198 may comprise a computer, a smart phone, a tablet, a laptop, a desktop, a wireless device, a wired device, a network device, a plurality of networked devices, a cloud computing environment, etc.

The memory 182 may include any of a variety of memory devices, such as using various types of computer readable or computer storage media. A computer storage medium or computer readable medium may be any medium that can contain or store the program for use by or in connection with the instruction execution system, apparatus, or device. By way of example, computer storage media may include dynamic random access memory (DRAM) or variants thereof, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data. Computer storage media generally includes at least one or more tangible media or devices. Computer storage media can, in some embodiments, include embodiments including entirely non-transitory components. In example embodiments, the computer storage medium is embodied as a computer storage device, such as a memory or mass storage device. In particular embodiments, the computer-readable media and computer storage media of the present disclosure comprise at least some tangible devices, and in specific embodiments such computer-readable media and computer storage media include exclusively non-transitory media. In the embodiment shown in FIG. 1A, the memory 182 stores a fracture face formation permeability framework 199.

The computing system 198 can also include a communication interface 186 configured to receive data, such as the sensor data from at least one sensor of the test sample analysis system 200. Other data may also be received via the communication interface 186. The communication interface 186 may also be configured to transmit data, or other functionality. The computing system 198 may also be configured to transmit notifications, calculations, etc. as generated by the framework 199, and the computing system 198 also includes a display 188 for presenting a user interface associated with the framework 199. For example, the framework 199 may be utilized for determining fracture face formation permeability, conductivity, or any combination thereof for viewing by one or more users via the display 188. In some embodiments, machine learning may even be utilized to perform some of the functionality, improve accuracy, etc. In various embodiments, the computing system 198 can include additional components, such as peripheral I/O devices, for example to allow a user to interact with the user interfaces generated by the framework 199. In various embodiments, the computing system 198 may also allow for interaction with at least one other software item, at least one other hardware item, at least one other storage items, or any combination thereof (including those from third parties) to carry out functionality.

Referring in particular to computing systems embodying the methods and systems of the present disclosure, it is noted that various computing systems can be used to perform the processes disclosed herein. For example, embodiments of the disclosure may be practiced in various types of electrical circuits comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, aspects of the methods described herein can be practiced within a general purpose computer or in any other circuits or systems.

Embodiments of the present disclosure can be implemented as a computer process (method), a computing system, or as an article of manufacture, such as a computer program product or computer readable media. The term computer readable media as used herein may include computer storage media. Computer storage media may include volatile and nonvolatile, removable and non-removable media implemented in any method or technology for storage of information, such as computer readable instructions, data structures, or program modules. Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing system 198, above. Computer storage media does not include a carrier wave or other propagated or modulated data signal. In some embodiments, the computer storage media includes at least some tangible features; in many embodiments, the computer storage media includes entirely non-transitory components.

Those of ordinary skill in the art will appreciate that various modifications may be made to the illustrated embodiments. For example, the wellbore 105 may simply be a vertical wellbore, instead of a horizontal wellbore, in a different embodiment. Examples of vertical wellbores are provided in U.S. Patent Application Publication No. 2014/0288909 and U.S. Patent Application Publication No. 2017/0058186), each of which is incorporated by reference in its entirety. Those of ordinary skill in the art will appreciate that not all of the illustrated components are mandatory in some embodiments. For example, one or both shims may be absent in a particular embodiment. Also, fluid may flow through the inlet1 201 and the inlet2 202 in some embodiments (e.g., as in FIG. 2N). Fluid may flow through the inlet1 201 and the inlet3 203 in some embodiments (e.g., as in FIG. 2O). Fluid may flow through the inlet1 201, the inlet2 202, and the inlet3 203 in some embodiments (e.g., as in FIG. 2P). The desired outcome may determine which inlets to utilize. The test sample analysis system 200 may be used in a laboratory setting, but it is not limited to a laboratory setting.

Figure 2T:
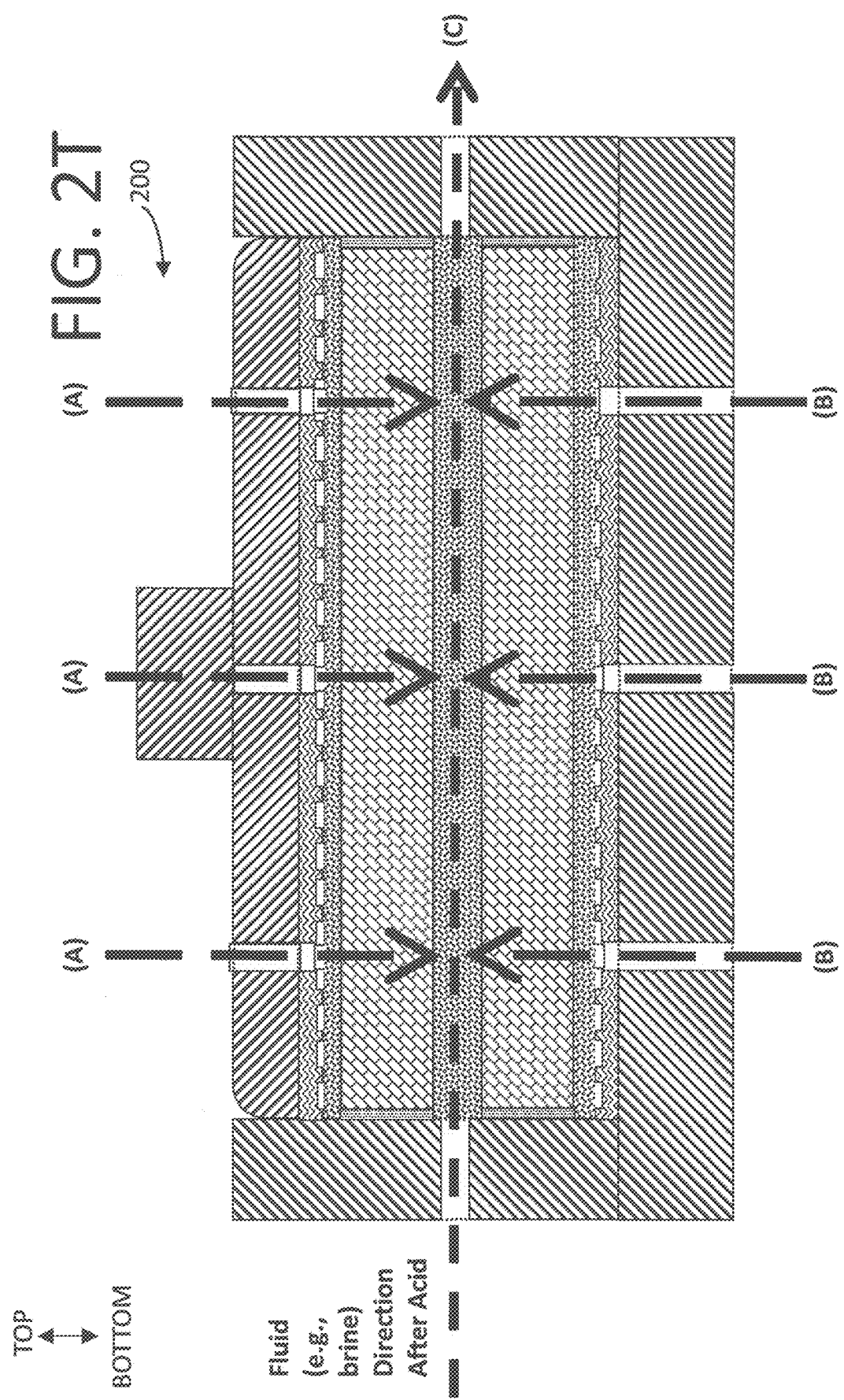
FIG. 2T illustrates one embodiment of the test sample analysis system flowing fluid (e.g., brine) after flowing fluid comprising acid.

Furthermore, the test sample analysis system 200 may be utilized when the fluid comprises acid. Additionally, the system 200 may be utilized for fluid (e.g., brine) after flowing acid. Some embodiments of the test sample analysis system flowing fluid comprising acid are illustrated in FIGS. 2S1, 2S2, and 2S3. One embodiment of the test sample analysis system flowing fluid (e.g., brine) after flowing fluid comprising acid is illustrated in FIG. 2T.

The description and illustration of embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

Moreover, while the invention has been described with reference to various embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. It is to be expressly understood, however, that each of the figures is provided for the purpose of illustration and description only and is not intended to limit the present invention.

The invention claimed is:

1. A system to analyze a test sample, comprising:
a housing having a cavity defined therein for holding a test sample;
a first inlet in fluid communication with the cavity to deliver fluid to the test sample;
a second inlet in fluid communication with the cavity to deliver fluid to the test sample, the first inlet configured to deliver fluid to the test sample in a direction substantially perpendicular to a direction that the second inlet is configured to deliver fluid to the test sample;
an outlet in fluid communication with the cavity to receive fluid from the test sample;
a force applicator configured to apply compressive force to the test sample within the cavity, wherein the force applicator forms a seal with the housing while applying compressive force to the test sample; and
at least one sensor configured to, while fluid flows from at least one of the inlets through the test sample to the outlet, determine a fluid characteristic, a test sample characteristic, or any combination thereof.

2. The system of claim 1, further comprising a first shim configured to distribute fluid delivered from the second inlet across a surface of the test sample.

3. The system of claim 1, further comprising a third inlet in fluid communication with the cavity to deliver fluid to the test sample, the third inlet configured to deliver fluid to the test sample in a direction substantially opposite of the direction that the second inlet is configured to deliver fluid to the test sample.

4. The system of claim 3, wherein the first inlet delivers fluid to a first side of the test sample, the second inlet delivers fluid to a top of the test sample, and the third inlet delivers fluid to a bottom of the test sample.

5. The system of claim 3, further comprising a second shim configured to distribute fluid delivered from the third inlet across a surface of the test sample.

6. The system of claim 1, wherein the test sample comprises at least one layer of porous media and at least one layer of proppant.

7. The system of claim 1, further comprising a first shim configured to distribute fluid delivered from the second inlet across a surface of the test sample, wherein the test sample comprises at least one layer of porous media and at least one layer of proppant, wherein the at least one layer of proppant is positioned between the at least one layer of porous media and the first shim.

8. The system of claim 1, further comprising a second shim configured to distribute fluid delivered from a third inlet across a second surface of the test sample, wherein the test sample comprises at least one layer of porous media and at least one layer of proppant, wherein the at least one layer of proppant is positioned between the at least one layer of porous media and the second shim.

9. The system of claim 1, wherein the test sample comprises at least one layer of porous media and at least one layer of proppant, wherein the at least one layer of proppant is positioned between a first layer of porous media and a second layer of porous media.

10. The system of claim 1, wherein at least a portion of an outer surface of the test sample is coated with epoxy such that the epoxy forms one or more seals between the outer surface of the test sample and the housing.

11. The system of claim 1, wherein the test sample comprises:
a first layer of proppant;
a second layer of proppant;
a first layer of porous media between the first and second layers of proppant;
a third layer of proppant; and
a second layer of porous media between the second and third layers of proppant.

12. The system of claim 1, further comprising at least one heating element configured to heat the test sample while fluid flows through the test sample.

13. The system of claim 1, wherein the fluid comprises brine, hydrocarbon, acid, gas, fracturing fluid, a single phase, multiple phases, or any combination thereof.

14. A method of analyzing a test sample, comprising:
flowing fluid through a test sample using a first fluid inlet and a fluid outlet;
flowing fluid through the test sample using another fluid inlet and the fluid outlet, wherein the first inlet is configured to deliver fluid to the test sample in a direction perpendicular to a direction that the other fluid inlet is configured to deliver fluid to the test sample;
applying a compressive force to the test sample while fluid flows through the test sample; and
while fluid flows from at least one of the inlets through the test sample to the fluid outlet, determining a fluid characteristic, a test sample characteristic, or any combination thereof.

15. The method of claim 14, wherein the other fluid inlet is a second fluid inlet only or a third fluid inlet only.

16. The method of claim 14, wherein the other fluid inlet comprises a second fluid inlet and a third fluid inlet.

17. The method of claim 14, further comprising determining a conductivity of the test sample using at least one determined characteristic.

18. The method of claim 14, further comprising determining a fracture face formation permeability of the test sample using at least one determined characteristic.

19. The method of claim 14, further comprising:
subsequently, flowing fluid through the first fluid inlet and the fluid outlet; and
determining conductivity using at least one determined characteristic.

20. The method of claim 19, wherein the test sample comprises layers of porous media and proppant, and the conductivity of the test sample accounts for proppant embedment within the porous media.

21. The method of claim 14, further comprising heating the test sample and fluid while fluid flows through the test sample.

22. The method of claim 14, wherein the fluid comprises brine, hydrocarbon, acid, gas, fracturing fluid, a single phase, multiple phases, or any combination thereof.

* * * * *